(12) United States Patent
Gardner

(10) Patent No.: US 10,758,708 B2
(45) Date of Patent: Sep. 1, 2020

(54) INTRODUCING STYLET

(71) Applicant: Glenn P. Gardner, Oak Brook, IL (US)

(72) Inventor: Glenn P. Gardner, Oak Brook, IL (US)

(*) Notice: Subject to any disclaimer, the term of this patent is extended or adjusted under 35 U.S.C. 154(b) by 0 days.

(21) Appl. No.: 16/671,474

(22) Filed: Nov. 1, 2019

(65) Prior Publication Data
US 2020/0139081 A1 May 7, 2020

Related U.S. Application Data

(60) Provisional application No. 62/916,386, filed on Oct. 17, 2019, provisional application No. 62/756,223, filed on Nov. 6, 2018.

(51) Int. Cl.
| | | |
|---|---|---|
| *A61M 25/01* | (2006.01) | |
| *A61M 16/04* | (2006.01) | |
| *A61B 1/05* | (2006.01) | |
| *A61B 1/00* | (2006.01) | |
| *A61B 1/267* | (2006.01) | |

(Continued)

(52) U.S. Cl.
CPC ..... *A61M 25/0102* (2013.01); *A61B 1/00045* (2013.01); *A61B 1/05* (2013.01); *A61B 1/267* (2013.01); *A61M 16/0429* (2014.02); *A61M 16/0488* (2013.01); *A61M 25/007* (2013.01); *A61M 25/0136* (2013.01); *A61M 25/0138* (2013.01); *A61M 2025/0006* (2013.01); *A61M 2025/1086* (2013.01); *A61M 2202/0208* (2013.01); *A61M 2205/0216* (2013.01); *A61M 2205/3569* (2013.01)

(58) Field of Classification Search
CPC ....... A61B 1/00045; A61B 1/05; A61B 1/267; A61M 16/0429; A61M 16/0488; A61M 16/04–0497; A61M 25/007; A61M 25/0102; A61M 25/0136; A61M 25/0138; A61M 25/005; A61M 25/0067; A61M 25/01; A61M 25/0133; A61M 25/0152; A61M 25/09; A61M 25/09016–09033; A61M 2025/0006; A61M 2025/1086; A61M 2025/0062; A61M 2025/0063; A61M 2202/0208; A61M 2205/0216; A61M 2205/3569
USPC .................................................. 600/120, 188
See application file for complete search history.

(56) References Cited

U.S. PATENT DOCUMENTS

| 4,502,482 A | * | 3/1985 | DeLuccia | ............. | A61M 16/04 |
| | | | | | 128/207.14 |
| 5,431,152 A | * | 7/1995 | Flam | .................... | A61B 1/2676 |
| | | | | | 600/120 |

(Continued)

FOREIGN PATENT DOCUMENTS

CN 209137662 U 7/2019

*Primary Examiner* — Justine R Yu
*Assistant Examiner* — Matthew D Ziegler
(74) *Attorney, Agent, or Firm* — MacMillan, Sobanski & Todd, LLC

(57) ABSTRACT

An introducing stylet is configured for insertion into an endotracheal tube (ETT) and includes an elongated rod having a distal end and a proximal end, and a positioning feature formed on the rod and configured to engage the ETT to prevent both longitudinal and lateral movement of the introducing stylet relative to the ETT. A portion of the distal end of the rod that extends longitudinally outwardly of the ETT and defines a leading end.

21 Claims, 14 Drawing Sheets

(51) Int. Cl.
*A61M 25/00* (2006.01)
*A61M 25/10* (2013.01)

(56) References Cited

U.S. PATENT DOCUMENTS

| | | | |
|---|---|---|---|
| 6,878,106 B1 * | 4/2005 | Herrmann | A61B 1/00073 |
| | | | 600/104 |
| 7,563,227 B2 | 7/2009 | Gardner | |
| 7,706,861 B2 * | 4/2010 | Windheuser | A61M 25/0097 |
| | | | 600/434 |
| 9,149,592 B2 * | 10/2015 | Roberts | A61M 16/0418 |
| 9,949,629 B2 | 4/2018 | Gardner | |
| 2003/0062039 A1 * | 4/2003 | Sniadach | A61M 16/0409 |
| | | | 128/200.26 |
| 2008/0110468 A1 * | 5/2008 | Nelson | A61M 16/0463 |
| | | | 128/207.15 |
| 2009/0050146 A1 * | 2/2009 | Smith | A61M 16/0488 |
| | | | 128/200.26 |
| 2013/0023729 A1 * | 1/2013 | Vazales | A61B 1/0669 |
| | | | 600/104 |
| 2017/0196445 A1 * | 7/2017 | Gardner | A61M 16/0434 |
| 2018/0169364 A1 * | 6/2018 | Jeffrey | A61M 16/0465 |
| 2018/0228992 A1 * | 8/2018 | Neame | A61M 16/0488 |

\* cited by examiner

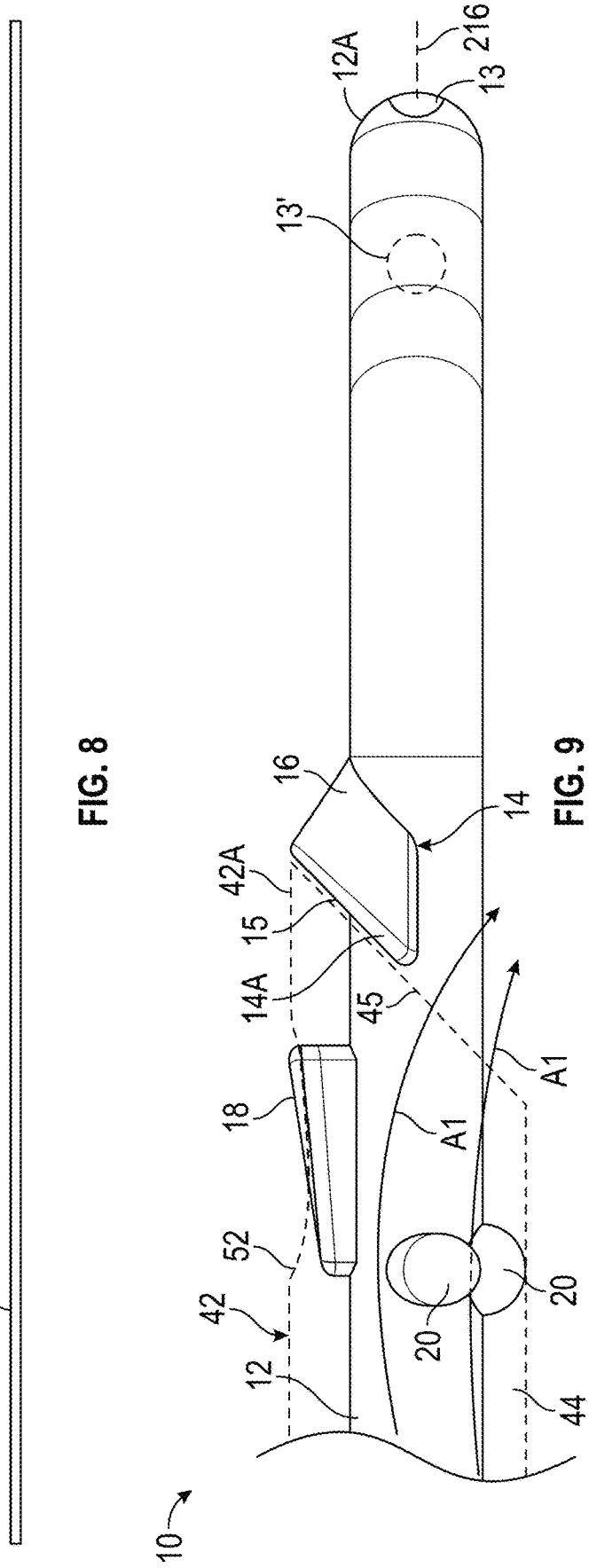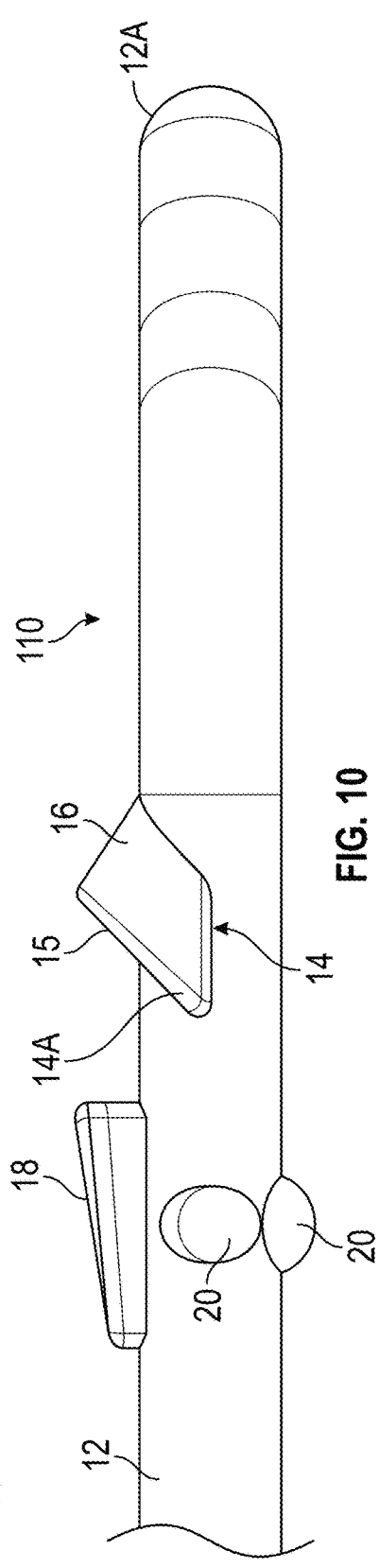

INTRODUCING STYLET

This invention relates in general to a device for introducing an intubation device, such as an endotracheal tube, into a patient. In particular, this invention relates to an improved introducing stylet, also known as an intubation assembly rod, configured to have an endotracheal tube (ETT) carried thereon.

Conventional endotracheal intubation is a three-step procedure including: (1) tissue retraction and separation, (2) vocal cord identification and visualization, and (3) endotracheal tube positioning, delivery, and passage.

Known endotracheal intubation devices address the first two steps well, such as with video-laryngoscopes and flexible fiberoptic and videoscopes. Unfortunately, despite good visualization the third step is still a challenge. For example, an operator may not be able to make the ETT reach, be positioned near, or adequately approach the vocal cords. The ETT may also become hung-up on laryngeal structures, such as the arytenoids, the vocal cords, and the cricoid cartilage or the anterior tracheal rings during attempts to pass the ETT through the larynx. Conventional tools such as bougies and rigid stylets do not fully solve the problem of positioning the ETT at the vocal cords, or ensuring smooth passage of the ETT through the larynx without becoming hung-up.

Despite proper tissue retraction and visualization of the vocal cords with currently available instruments such as a direct laryngoscope, indirect video laryngoscope, or a flexible videoscope, the delivery, placement, and passage of the endotracheal tube is often challenging. Stiff, rigid, and potentially traumatic stylets are frequently shaped and placed within the endotracheal tube, to give more control and guidance to the endotracheal tube tip in the direction of the visualized vocal cords. However, once the rigid stylet has been manually shaped, the user must work with that specific curvature and shape. If the curvature and shape is not satisfactory, the user must stop the laryngoscopy, remove all of the equipment, manually reshape the stylet, and start the procedure over from the beginning.

It is often the case with flexible videoscopes, flexible fiber-optic bronchoscopes, and rigid direct or indirect laryngoscopes, that visualization of the vocal cords may be achieved wherein placement of the endotracheal tube tip is at the vocal cords, or the flexible scope is within the trachea, but the passage of the endotracheal tube tip through the larynx between the vocal cords and into the trachea is obstructed. The leading edge of the endotracheal tube tip often collides with laryngeal structures, such as the arytenoids, the cricoid cartilage, or the anterior wall of the trachea, preventing smooth passage of the endotracheal tube into the trachea.

ETT introducers, bougies, and tube exchangers act as guides for the delivery of an endotracheal tube into the trachea. These guides are typically significantly smaller in diameter and longer in length than the ETT that they will be guiding. Bougies will have a degree of angulation at their distal end, otherwise these guides are semi-rigid cylinders or rods. After direct laryngoscopy or indirect video laryngoscopy, the introducer or bougie is passed under visual guidance control, blindly under the epiglottis, or sometimes aided by the tactile feel of rubbing the tip along the anterior tracheal rings.

Once the introducer, tube exchanger, or bougie is successfully placed well into the trachea, the laryngoscopy is either repeated or continued and the ETT is then railroaded or threaded over the guide and into the trachea. These additional steps may be time consuming and delay intubation. During the railroading step an operator may encounter difficulty in passage due to the ETT tip colliding with the arytenoids, cricoid ring, or anterior tracheal ring. This obstruction of ETT passage is largely due to a gap between an outer wall of the guide and an inner wall of the ETT, as well as an unfavorable angle of ETT entry into the trachea. This difference in diameter and resultant gap may cause the leading edges of the ETT to hang up on structures of the larynx such as the arytenoids or vocal cords during passage. The natural curvature of the ETT leads to an unfavorable angle of entry leading to obstruction of passage on the cricoid and anterior tracheal rings. This then requires the operator to rotate the ETT about 90 degrees one or more times until the ETT smoothly passes into the trachea. Excessive force should be avoided as such force may cause trauma and harm to the structures of the larynx.

Conventional ETT stylets are semi-rigid, malleable or stiff rigid rods that help shape the ETT to help control its direction toward the vocal cords and trachea. Their leading tips do not extend distally of the ETT when in use as their size, shape and rigidity may easily traumatize or damage the vocal cords, trachea, or other laryngeal structures. Despite being placed properly within an ETT, the stylet should be removed precisely prior to passage thru the vocal cords and into the trachea due to potential trauma from the improved rigidity of the inserted stylet. This removal step requires perfect timing and often additional skilled staff.

It would therefore be desirable to provide an improved introducing stylet configured to have an ETT carried thereon for introducing the ETT into a patient.

SUMMARY OF THE INVENTION

This invention relates to an improved structure for an introducing stylet for introducing an endotracheal tube (ETT) into a patient. The improved introducing stylet is configured to have an ETT carried thereon.

In a first embodiment, an introducing stylet is configured for insertion into an endotracheal tube (ETT) and includes an elongated rod having a distal end and a proximal end, and a positioning feature formed on the rod and configured to engage the ETT to prevent both longitudinal and lateral movement of the introducing stylet relative to the ETT. A portion of the distal end of the rod that extends longitudinally outwardly of the ETT and defines a leading end.

In a second embodiment, the introducing stylet is configured for insertion into an ETT and includes an elongated rod having a distal end and a proximal end. A bridge extending radially outward of the rod at the distal end thereof and proximal of a distal tip of the ETT into which the introducing stylet has been inserted. The introducing stylet also includes an elongated, malleable rod within a longitudinally extending bore, and an obturating feature extending circumferentially about a portion of the rod and including a tapered leading surface, a flat trailing surface, and an arcuate edge formed between the leading surface and the trailing surface and defining an ETT-engaging surface. The obturating feature is configured to occlude a gap that would otherwise exist between a flat leading surface of a bevel of the ETT and the obturating feature, and to occlude a gap that would otherwise exist between a portion of an inside surface of a distal end of the ETT and the obturating feature. The introducing stylet additionally includes a Murphy eye plug, and an oxygen source cap mounted to a 15 mm ETT connector of the ETT. The oxygen source cap includes a body having circumferentially extending wall defining a generally cylindrical outside surface, a first end, an open second end, and means to releasably attach the oxygen source cap to the 15 mm ETT connector. A cylindrical air inlet extends radially outward of the circumferentially extending wall, wherein the air inlet is in fluid communication with the open second end of the oxygen source cap and is configured for connection to source of oxygen. A portion of the distal end of the rod that extends longitudinally outwardly of the positioning feature defines a leading end formed with two bends defining a soft S-shape. The bridge is configured to engage an inside surface of the ETT to prevent both longitudinal and lateral movement of the introducing stylet relative to the ETT.

Various aspects of this invention will become apparent to those skilled in the art from the following detailed description of the preferred embodiments, when read in light of the accompanying drawings.

BRIEF DESCRIPTION OF THE DRAWINGS

FIG. 8. is a plan view of an introducing stylet core used with the introducing stylet illustrated in FIGS. 1 through 7.

FIG. 9 is an enlarged view of the distal end of the introducing stylet illustrated in FIG. 3.

FIG. 10 is an enlarged view of the distal end of a second embodiment of the introducing stylet illustrated in FIGS. 1 through 9.

DETAILED DESCRIPTION OF THE PREFERRED EMBODIMENTS

Figure 1:
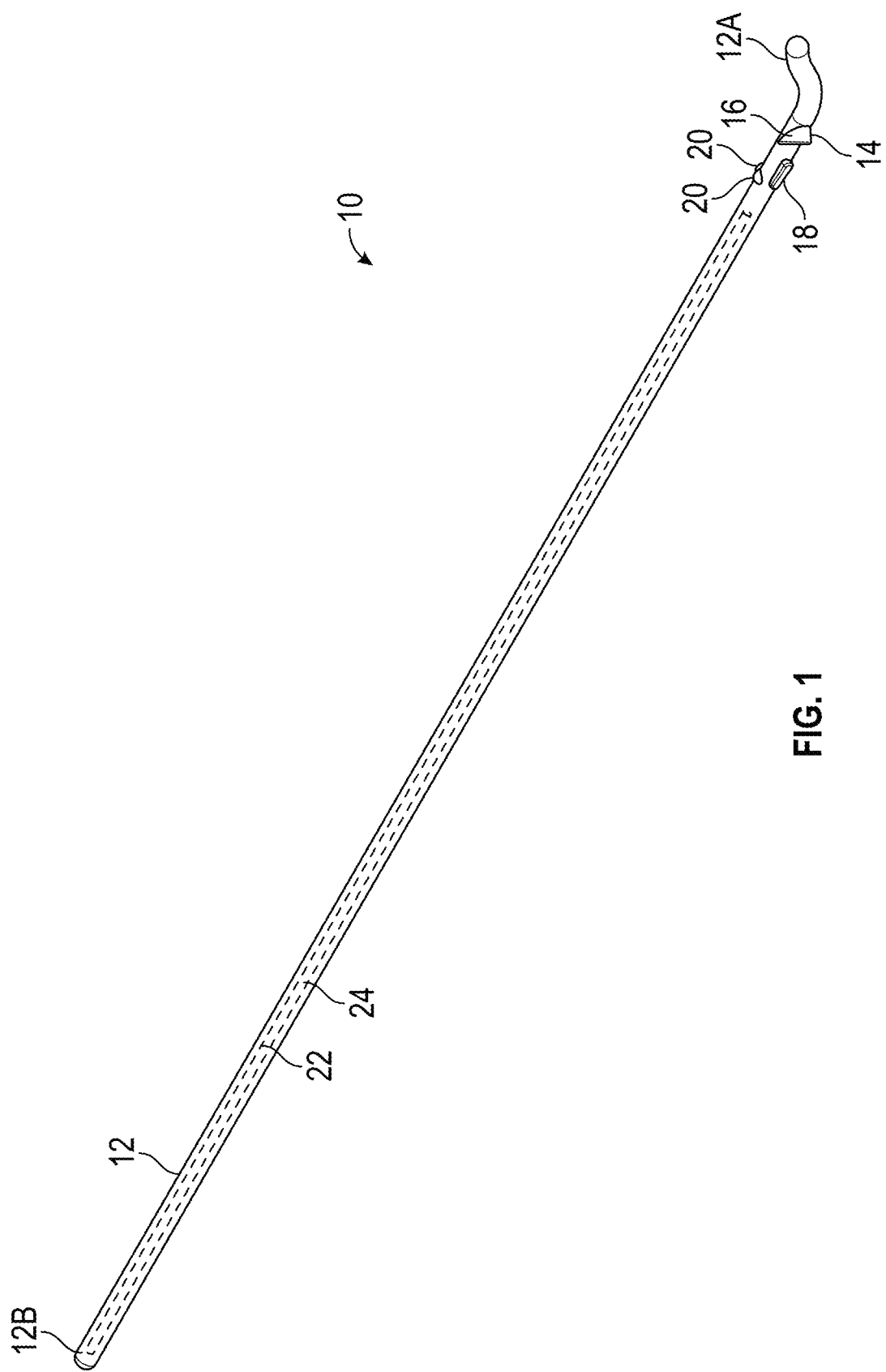
FIG. 1 is a perspective view of a first embodiment of introducing stylet according to this invention.

The present invention will now be described with occasional reference to the specific embodiments of the invention. This invention may, however, be embodied in different forms and should not be construed as limited to the embodiments set forth herein. Rather, these embodiments are provided so that this disclosure will be thorough and complete, and will fully convey the scope of the invention to those skilled in the art.

Referring now to the drawings, a first embodiment of an introducing stylet is indicated at 10 in FIGS. 1 through 7. The introducing stylet 10 includes an elongated body configured as a rod 12. The rod 12 is substantially cylindrical and has a first or distal end 12A and a second or proximal end 12B. Alternatively, the rod 12 may have any other desired cross-sectional shape, including but not limited to substantially oval, substantially hexagonal, and substantially rectangular. The distal end 12A of the illustrated rod 12 has a soft S-shape as best shown in FIGS. 1, 2, 6, 7, and 12. It will be understood that the distal end 12A of the rod 12 of the introducing stylet 10 may have a shape other than the illustrated soft S-shape. For example, the distal end 12A may be substantially straight, may have one bend or more than the two bends illustrated. The bends may be formed in any radial direction.

A distal tip of the distal end 12A of the illustrated introducing stylet 10 is rounded, such as having a semi-spherical shape. Advantageously, this rounded or semi-spherical shape of the distal end 12A thus defines an atraumatic, blunt tip that is configured to be non-piercing when introduced into the patient. It will be understood that the distal end 12A may have other shapes, such as tapered, conical, or having a ball-shaped tip. These tip shapes may assist the user by providing improved tactile feel when inserting the introducing stylet 10 into a patient. If desired, one or more tactile members may be formed on or near one or more of the bends in the distal end 12A. One example of such a tactile member is shown at 19 in FIG. 12. The exemplary tactile member 19 is semi-spherical in shape. However, it will be understood that the tactile member 19 may have any other desired shape configured to improve the tactile feel of the user when introducing the introducing stylet 10 into a patient.

Figures 16, 16A:
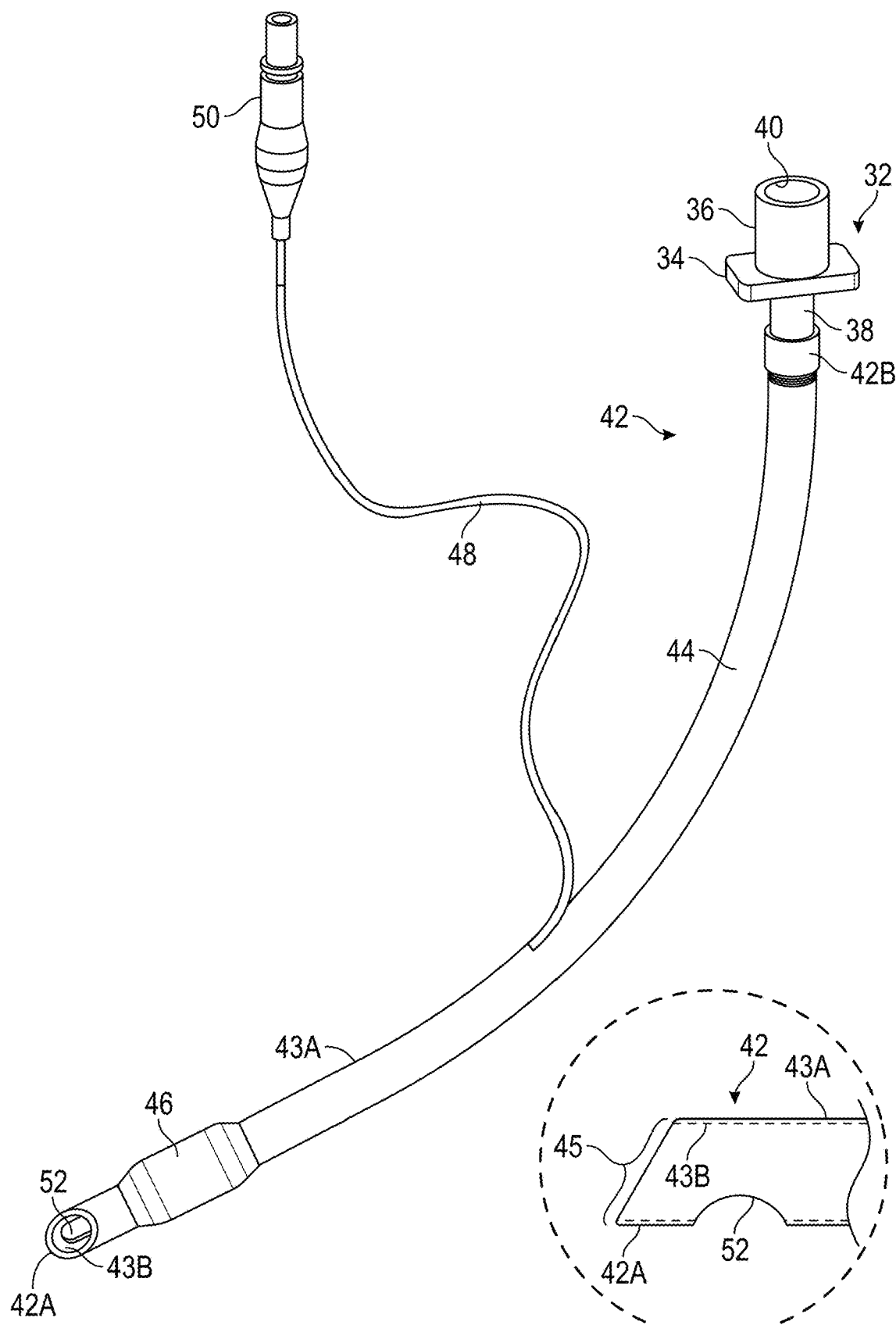
FIG. 16 is a perspective view of a conventional ETT, a portion of which is shown in FIG. 9.
FIG. 16A is an enlarged view of the distal end of the ETT illustrated in FIG. 16.

In the illustrated embodiment, the introducing stylet 10 is shown prior to being inserted into a conventional endotracheal tube (ETT), such as the conventional ETT 42 shown in FIG. 16. Thus, the introducing stylet 10 is configured to have the ETT 42 mounted thereon, and together define an introducing stylet assembly. As best shown in FIG. 9, a portion of the distal end 12A of the rod 12 that extends longitudinally outwardly, i.e., distally, of a distal end 42A of the ETT 42 defines a leading end of the rod 12.

As shown in FIGS. 16 and 16A, the conventional ETT 42 has the first or distal end 42A, a second or proximal end 42B, and an ETT body 44 configured as a transparent tube. A balloon cuff 46 is formed at the distal end 42A of the ETT 42 and a conventional 15 mm ETT connector 32 is removably attached to the ETT body 44 at the proximal end 42B thereof. It will be understood that conventional ETTs include the conventional 15 mm ETT connector 32 removably attached to the proximal ends 42B thereof. A conventional Murphy eye 52 is formed between the balloon cuff 46 and the distal end 42A. An air inflation tube 48 has a distal end attached to the balloon cuff 46 and a connector 50 at a proximal end thereof configured for attachment to a source of air, such as a syringe (not shown). The distal end 42A is configured as a bevel having a substantially flat surface, i.e., a surface within a single plane, best shown at 45 in FIG. 16A, such that the distal end 42A has a sharp or spear-like shape. It will be understood that the ETT 42 may be any conventional pediatric or adult ETT and thus may have a wall thickness within the range of about 0.5 mm to about 1.5 mm.

Advantageously, the illustrated introducing stylet 10 includes a first or overhanging obturating feature 14. The exemplary overhanging obturating feature 14 extends circumferentially about 180 degrees around the rod 12 and includes a tapered leading surface 16 and a substantially flat trailing surface 15. The leading surface 16 is tapered longitudinally and radially outwardly from its distal end to its proximal end to prevent hang-ups and to facilitate insertion of the introducing stylet 10 into the ETT 42. An arcuate edge is defined between the leading surface 16 and the trailing surface 15 and defines an ETT-engaging surface 14A.

As best shown in FIG. 9, the overhanging obturating feature 14 is configured to occlude or close a gap that would otherwise exist between a leading portion of the surface of the bevel 45 of the ETT 42 and the trailing surface 15 of the overhanging obturating feature 14. It will be understood that the overhanging obturating feature 14 may also be configured other than the illustrated overhanging obturating feature 14. For example, the overhanging obturating feature 14 may have any desired shape or size such that it extends radially outwardly from a longitudinal axis 216 of the introducing stylet 10 and is configured to occlude or close the gap that would otherwise exist between a portion of the overhanging obturating feature 14, such as the ETT-engaging surface 14A, and an inside surface 43B of the ETT 42, such as when the overhanging obturating feature 14 is positioned inside the distal end 42A of the ETT 42.

Figure 11:
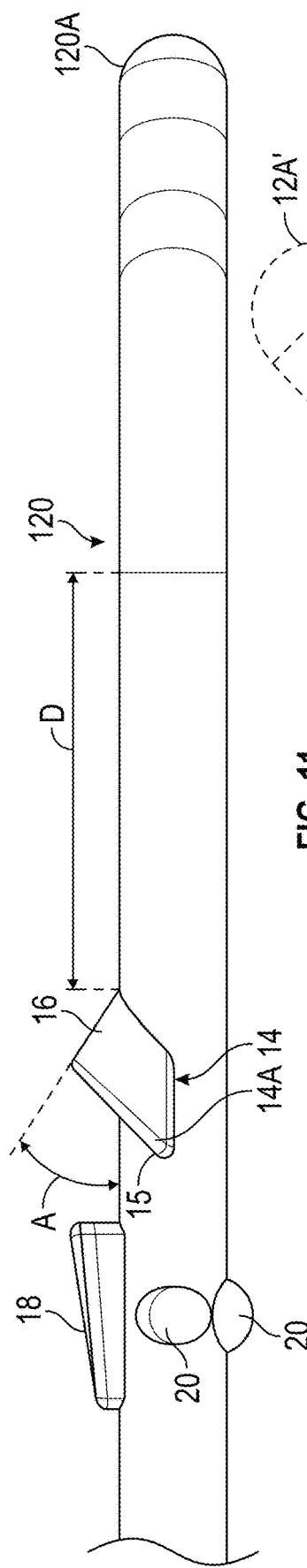
FIG. 11 is an enlarged view of the distal end of a third embodiment of the introducing stylet illustrated in FIGS. 1 through 9.

As shown in FIG. 11, the leading surface 16 of the overhanging obturating feature 14 is formed at an angle A of about 45 degrees from an outside surface of the rod 120. Alternatively, the leading surface 16 of the overhanging obturating feature 14 may be formed at an angle A within the range of about 15 degrees to about 60 degrees. Additionally, the leading surface 16 of the overhanging obturating feature 14 may be formed at the angle A within the range of about 5 degrees to about 85 degrees.

If desired, the overhanging obturating feature 14 may have other shapes and may be configured to be hollow, inflatable, or compressible. For example, the overhanging obturating feature 14 may be configured as a hollow inflatable portion of the introducing stylet 10. Alternatively, the overhanging obturating feature 14 may be formed of any gel-like or other substantially soft material designed to compressible or semi-compressible.

Figure 22:
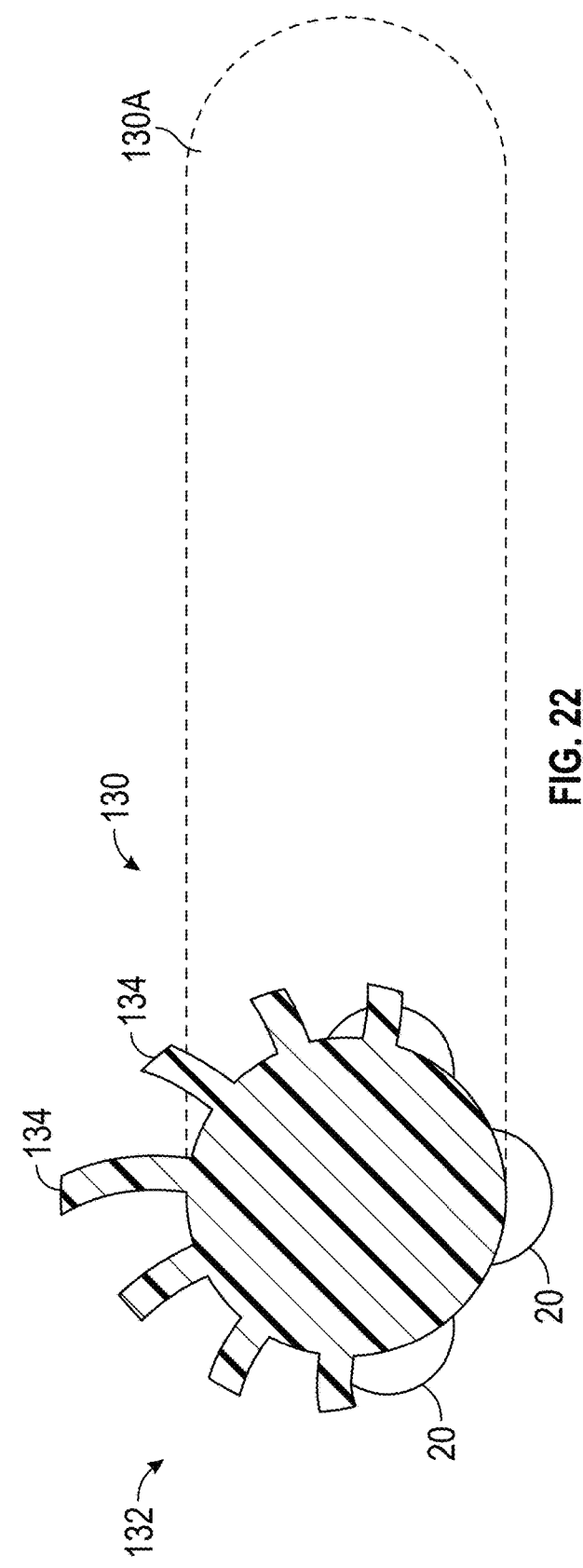
FIG. 22 is a cross-sectional view of an alternate embodiment of the introducing stylet illustrated in FIG. 5 showing the obturating feature formed from ribs.

Additionally, the obturating feature may include ribs. For example, FIG. 22 illustrates an alternate embodiment of the introducing stylet 130 having a distal end 130A and an obturating feature 132 formed from ribs 134. The obturating feature 132 is thus be compressible. Like the ribs 28 shown FIGS. 13 and 14, the plurality of ribs 134 extend longitudinally and radially outwardly of the elongated body of the introducing stylet 130. As shown in FIG. 22, the ribs 134 have an arcuate cross-sectional shape. Alternatively, the ribs 134 may have a non-arcuate cross-sectional shape, such as substantially straight.

Figure 23:
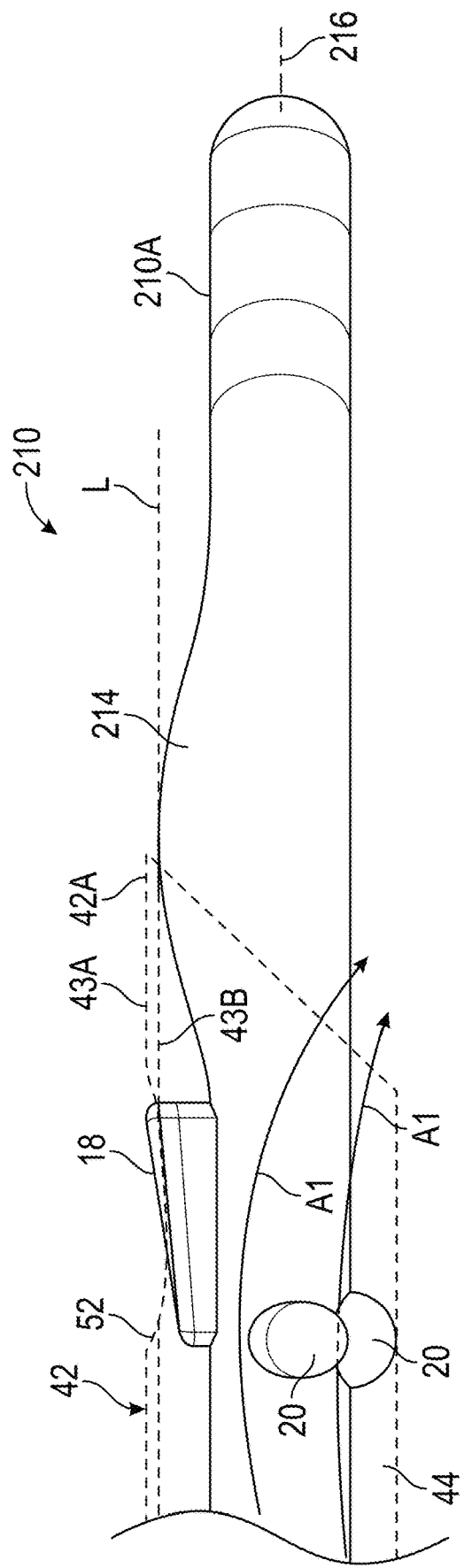
FIG. 23 is an enlarged view of the distal end of an alternate embodiment of the introducing stylet showing the overhang feature.

It will be understood in lieu of the overhanging obturating feature 14, the introducing stylet may be formed with a second obturating feature 214, such as shown in the introducing stylet 210 having the distal end 210A, illustrated in FIG. 23. The second obturating feature 214 is configured as a rounded protruding portion, the widest point of which, i.e., the portion that extends the greatest distance transversely from the axis 216 of the introducing stylet 210, does not extend transversely outward of the inside surface 43B of the ETT 42, or beyond a line L extending longitudinally outward from the inside surface 43B. Preferably, the second obturating feature 214 engages or abuts the inside surface 43B of the ETT 42. Alternatively, if desired, the second obturating feature 214 may extend radially outwardly beyond an outside surface 43A of the ETT 42. The introducing stylet 210 may also include a Murphy eye plug 18 and one or more bridges 20, as described below.

Advantageously, both the overhanging obturating feature 14 and the second obturating feature 214 cooperate with the ETT 42 to block or blunt the distal end 42A of the ETT 42, therefore mitigating the potentially negative effects of the sharp or spear-like shape of the distal end 42A by providing a rounded or otherwise non-sharp feature at the distal end 42A of the ETT 42 when mounted on the introducing stylets 10, 210 during insertion into a patient. Thus, the rounded or otherwise non-sharp feature at the distal end 42A of the ETT 42 provided by the overhanging obturating feature 14 and the second obturating feature 214 combines with the rounded or semi-spherical shape of the distal ends 12A and 210A, respectively, to define an atraumatic, blunt tip and an atraumatic, blunt leading end for the ETT 42 that are deflected off of the arytenoids, the vocal cords, the rima glottidis, and the cricoid cartilage or the anterior tracheal rings to minimize the possibility of trauma or piercing that may be caused by the distal end 12A of the introducing stylet 10 and/or the spear-like shape of the distal end 42A if caught or otherwise hung-up when the introducing stylet 10 is being advanced into the trachea.

The Murphy eye plug 18 is formed proximal of the overhanging obturating feature 14. The Murphy eye plug 18 is elongated and configured to be positioned within a Murphy eye 52 of the conventional ETT 42. When positioned within the Murphy eye 52, the Murphy eye plug 18 is configured to significantly minimize or prevent longitudinal movement of introducing stylet 10. It will be understood that the Murphy eye plug 18 may be formed other than as illustrated and may not be continuous from its distal end to its proximal end. For example, the Murphy eye plug 18 may be segmented or fragmented from its distal end to its proximal end such that the Murphy eye plug 18 comprises two or more segments.

The illustrated Murphy eye plug 18 is tapered longitudinally and radially inwardly from its distal end to its proximal end to facilitate removal of the introducing stylet 10 from the ETT 42 after the ETT 42 has been inserted into the patient. It will be understood however, that the Murphy eye plug 18 need not be tapered. For example, a tapered Murphy eye plug may not be required if the Murphy eye plug 18 is rotated such that it is positioned within the ETT 42 at a location other than within the Murphy eye 52.

In the illustrated embodiment, the Murphy eye plug 18 has an overall length at least slightly smaller than a length of the conventional Murphy eye 52 of the ETT 42. The leading edge (the right-most edge when viewing FIGS. 9 through 11) may have any desired height. The illustrated leading edge has a height of about 2.372 mm. Alternatively, the Murphy eye plug 18 may have a height within the range of about the thickness of the wall of a conventional pediatric or adult ETT to about 4.0 mm.

Figure 15:
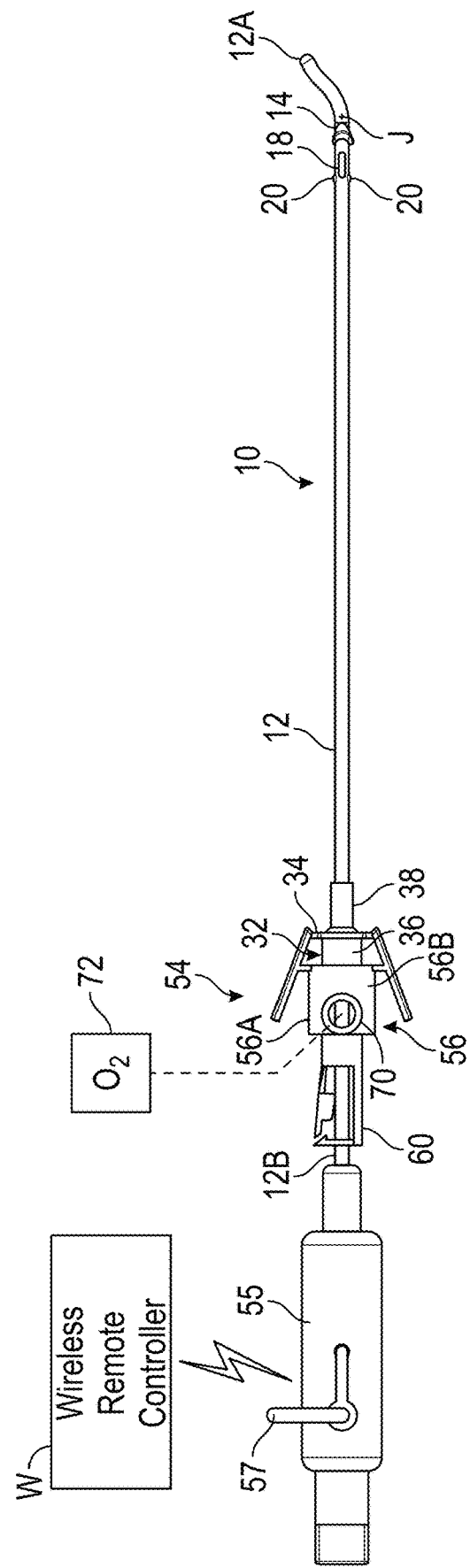
FIG. 15 is a right side view of the introducing stylet illustrated in FIG. 2 shown with an ETT connector and an oxygen source cap mounted thereto.

In the embodiments of the introducing stylets illustrated and described herein, one Murphy eye plug 18 is shown formed at the distal end of the introducing stylet (on the right side when being inserted by an operator; see also the right side view of the introducing stylet 10 illustrated in FIG. 15). It will be understood that the one Murphy eye plug 18 may be formed on the left side of the introducing stylet 10, i.e. at about 180 degrees from the Murphy eye plug 18 shown in FIGS. 1 through 13 and 15. Alternatively, any of the introducing stylets illustrated and described herein may have two or more Murphy eye plugs 18 formed thereon. For example, if the introducing stylet is used with a conventional Parker endotracheal tube that has two Murphy eyes 52, two Murphy eye plugs 18 may be advantageous to position the ETT radially and longitudinally relative to the introducing stylet.

In the illustrated embodiments, one or more semi-spherical bridges 20 extend radially outwardly from the rod 12 and are configured to engage an inside surface of the ETT 42 to significantly minimize or prevent lateral movement of overhanging obturating feature 14, i.e., movement of the overhanging obturating feature 14 away from the inside surface of the distal end 42A of the ETT 42. The bridges 20 further define air flow paths as shown by the arrows A1 in FIGS. 9 and 23 to ensure that air flow is maintained around the one or more bridges 20 and between the bridges 20 and the rod 12 opposite the overhanging obturating feature 14. In the illustrated embodiment, three bridges 20 are shown positioned radially at about 90 degrees, 180 degrees, and 270 degrees from a center of the Murphy eye plug 18.

Figure 24:
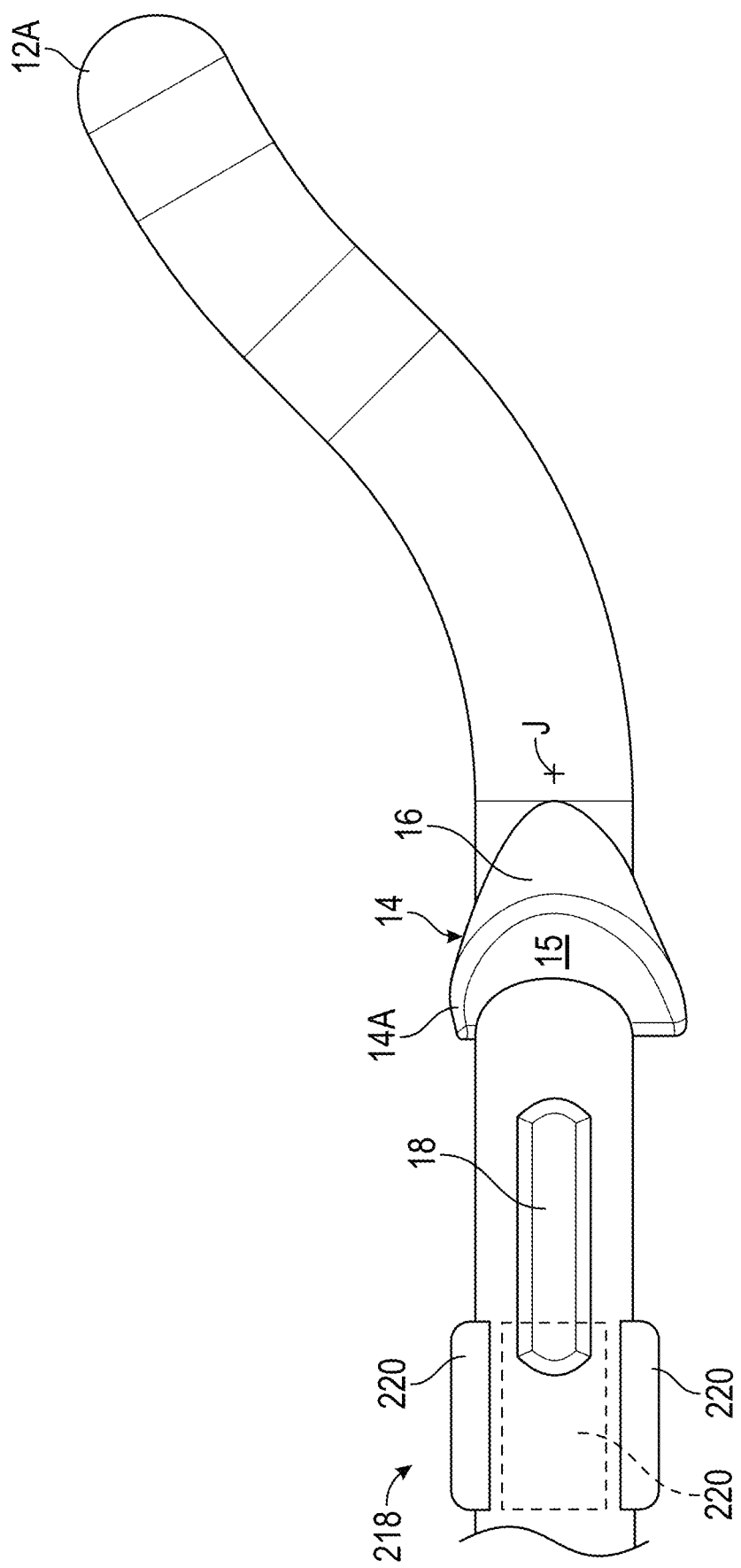
FIG. 24 is an enlarged top plan view of the distal end of an alternate embodiment of the introducing stylet showing the elongated bridges.

Alternatively, the bridges 20 may be formed as any structure or combination of structures that extend radially outwardly from the rod 12 and are configured to engage an inside surface of the ETT 42 to support, secure, and stabilize the position of the ETT 42 on the introducing stylet 10 so as to significantly minimize or prevent lateral movement of overhanging obturating feature 14. Additionally, the bridges 20 may formed as any elongated structure or structures that extend radially outwardly from the rod 12 and extend longitudinally along the rod 12, such as the bridges 220 shown in the embodiment of the introducing stylet 218 shown in FIG. 24. The bridges 220 may be formed having any desired length and may be formed at any desired location along the length of the introducing stylet 10. Also, the ribs 28, described below, may function as bridges.

As also shown in FIG. 9, the introducing stylet 10 may be formed with a video imaging device in the distal tip thereof, such as shown at 13. Alternatively, the video imaging device 13 may be positioned at any desired location of the leading end of the introducing stylet 10 from the overhanging obturating feature 14 to the distal end 12A of the introducing stylet 10, as shown at 13' in FIG. 9. The video imaging device 13 may be any desired video imaging device, such as a Complementary Metal Oxide Silicon (CMOS) camera, a Charge-Coupled Device (CCD), fiber optic camera, and any other direct or indirect imaging device. Accordingly, an electrical wire (not shown) for an imaging device such as the CCD may extend longitudinally within introducing stylet 10. The video imaging device 13 is operationally connected, for example either wired or wirelessly connected, to a monitor, such as the video monitor 240.

Figure 21:
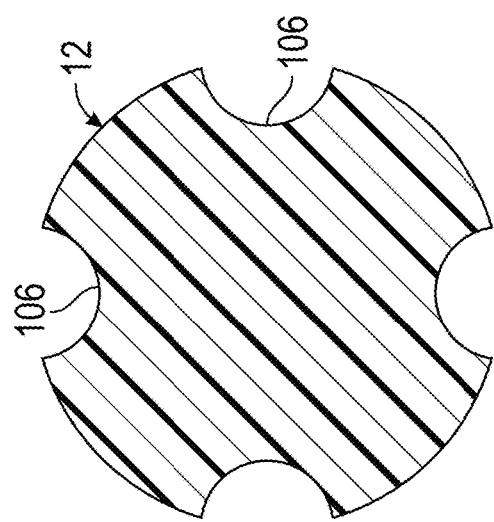
FIG. 21 is a cross-sectional view of the introducing stylet illustrated in FIGS. 1 through 9 showing the longitudinal grooves formed in an outside surface thereof.

It will be understood that the rod 12 of the introducing stylet 10 may have any size, shape, feature, or combination of sizes, shapes, and features configured to allow air flow around the introducing stylet 10 from the proximal end 12B to the distal end 12A. For example, the rod 12 may have one or more longitudinal grooves 106 formed in an outside surface thereof, as shown in FIG. 21.

It will be further understood that each of the overhanging obturating feature 14, the Murphy eye plug 18, and the plurality of semi-spherical bridges 20 may function as positioning features for the ETT 42 mounted thereon, as described below.

For example, when functioning as a positioning feature, the overhanging obturating feature 14, the Murphy eye plug 18, and the plurality of semi-spherical bridges 20, individually or in combination, are configured and positioned to engage the inside surface of the ETT to significantly minimize or prevent both longitudinal and lateral movement of the introducing stylet 10 relative to the ETT 42. Additionally, when functioning as a positioning feature, the overhanging obturating feature 14, the Murphy eye plug 18, and the plurality of semi-spherical bridges 20, the air flow paths A1 are defined adjacent the overhanging obturating feature 14, the Murphy eye plug 18, and the plurality of semi-spherical bridges 20 between the inside surface of the ETT 42 and the respective overhanging obturating feature 14, Murphy eye plug 18, and plurality of semi-spherical bridges 20. The air flow paths A1 thus ensure that air flow is maintained through the ETT 42.

A handle, such as the handle 55 described below, may include a processor or controller (not shown) with Wi-Fi, or local area wireless technology that allows the introducing stylet 10 to participate in computer networking. The processor or controller (not shown) may also have Bluetooth capability to allow a medical specialist to view any video images captured by the video imaging device 13 on an attached or remotely located screen via the internet or any wireless means of communication. If desired, the processor or controller (not shown) may be located at any desired location of the rod 12 of the introducing stylet 10.

Figure 6:
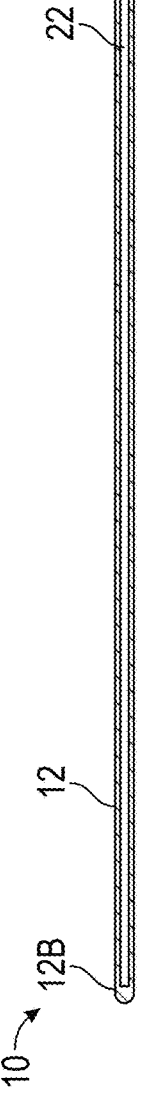
FIG. 6 is a cross-sectional view taken along the line 6-6 of FIG. 3.
Figure 7:
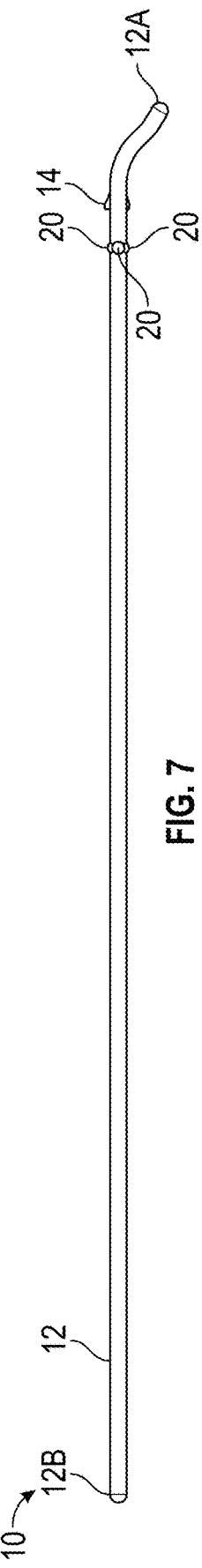
FIG. 7 is a left side view of the introducing stylet illustrated in FIGS. 1 through 6.

The introducing stylet 10, including the distal end 12A thereof may be formed from any flexible, semi-flexible, malleable, or compressible material, such as silicon, rubber, polyvinylchloride (PVC), polyurethane, and other polymers. Thus, the distal end 12A is configured with advantageous flexibility when inserted into a patient's airway. It may be desirable however for a body of the rod 12, e.g., the portion of the rod 12 proximal of the obturator feature 14 or the leading end of the rod 12 to be relatively rigid and malleable. As shown in FIG. 6, the introducing stylet 10 may therefore have a longitudinally extending bore 22 formed therein. An elongated aluminum rod 24, shown in FIG. 8, may be mounted within the bore 22 to provide the desired rigidity. Thus, the bore 22 and the aluminum rod 24 may extend into the leading end of the rod 12, including to a distal tip of the distal end 12A. Alternatively, any desired portion of the introducing stylet 10, for example, the proximal end 12B thereof, may be expandable, such as formed with telescoping sections (not shown).

In the illustrated embodiment, the introducing stylet 10 has an overall length of about 46 cm. Alternatively, the introducing stylet 10 may have any other desired length.

In the illustrated embodiment, the introducing stylet 10 has an outside diameter of about 5.5 mm. Alternatively, the introducing stylet 10 may have any desired outside diameter, such as within the range of about 1.0 mm to about 8.0 mm so as to be used with conventional pediatric and adult ETTs.

In the illustrated embodiment, the bore 22 of the introducing stylet 10 has an overall length of about 39.5 cm and a bore diameter about 2.38 mm. Alternatively, the bore 22 may have any other desired length and any other desired bore diameter, such as but not limited to 1.6 mm.

In the illustrated embodiment, the aluminum rod 24 has an overall length of about 39.5 cm and an outside diameter about 2.381 mm. Alternatively, the aluminum rod 24 may have any other desired length and any other desired, outside diameter. The rod 24 has been described as being formed from aluminum. It will be understood however, that the rod 24 may be formed from any other non-malleable, rigid, semi-rigid, flexible, semi-flexible, or malleable material. As used herein, malleable is defined as a metal or other material that is able to be bent or otherwise shaped and reshaped without breaking or cracking and having shape memory, wherein the shape into which the malleable material has been bent is retained until it has been again bent or shaped. For example, the proximal end 12B of the rod 12 may be bent by the user to prevent rearward movement of the ETT 42, i.e., movement of the ETT 42 toward the proximal end 12B of the rod 12, and to thus provide proximal and longitudinal position support for the ETT 42 on the introducing stylet 10.

In the illustrated embodiment, the bridges 20 have a radius of about 1.0 mm and extend radially outwardly from the rod 12 about 1.0 mm. Alternatively, the bridges 20 may have any desired radius. Preferably, the bridges 20 may extend outwardly from the rod 12 a distance such that the bridges 20 engage or abut, or are positioned very close to, the inside surface of the ETT 42 to significantly minimize or prevent lateral movement of the ETT 42, i.e., movement generally perpendicular to a longitudinal axis of the rod 12.

Advantageously, the flexibility, and the curved shape of the distal end 12A (i.e., the soft S-shape of the distal end 12 in the illustrated embodiment), and rounded or semi-spherical shape of the distal end 12A combine to improve direction of delivery, and to thus control the distal end 12 of the introducing stylet 10 such that it may be deflected off of the arytenoids, the vocal cords, the rima glottidis, and the cricoid cartilage or the anterior tracheal rings to minimize the possibility of trauma or piercing that may be caused by the distal end 12A of the introducing stylet 10 if caught or otherwise hung-up when the introducing stylet 10 is being advanced into the trachea.

Figure 12:
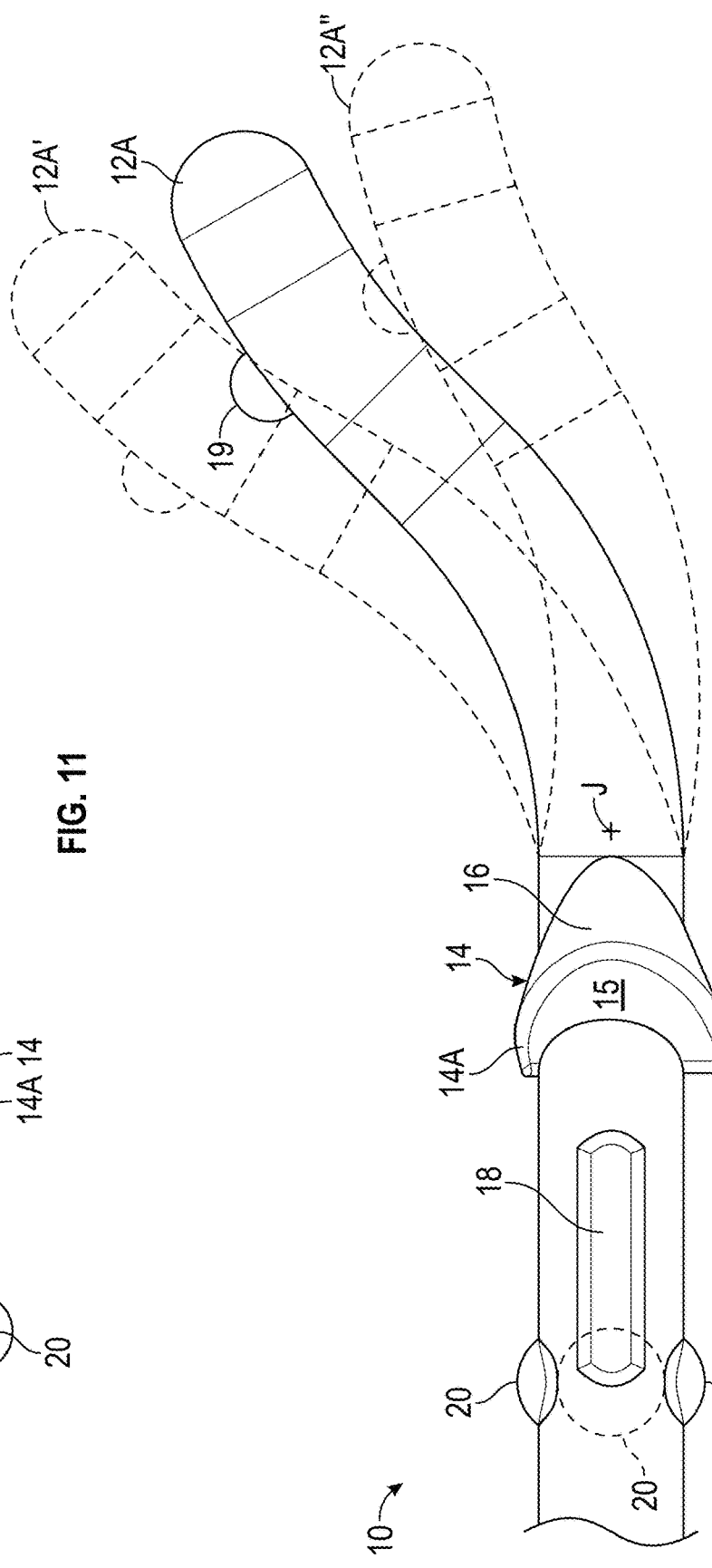
FIG. 12 is an enlarged top plan view of the distal end of the introducing stylet illustrated in FIG. 9.

The distal end 12A of the introducing stylet 10 may be articulating so as to be configured to move in any radial direction, thus a joint J may be configured as an articulating joint, as illustrated in FIG. 12. In the embodiment of the introducing stylet 10 illustrated in FIG. 12, the articulating joint J is preferably located adjacent and distal of the overhanging obturating feature 14, thus allowing the user to more accurately control the distal end 12A of the introducing stylet 10, so as to move the distal end 12A between a plurality of alternate, i.e., articulated positions, such as the positions shown at 12A' and 12A". Alternatively, one or more of the articulating joints J may be located at any other location or locations on the introducing stylet 10.

Figure 18:
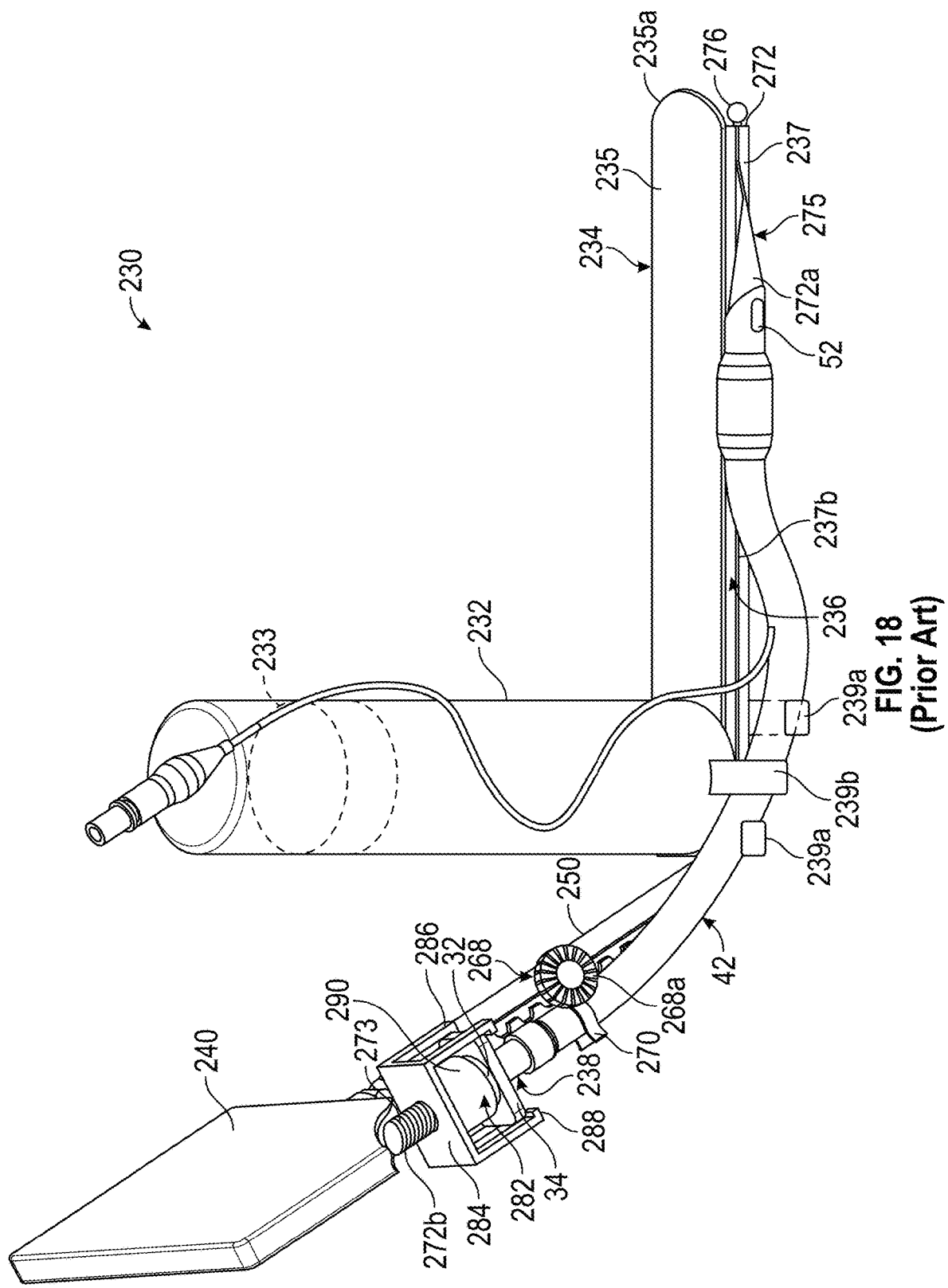
FIG. 18 is a perspective view of an embodiment of a known endotracheal tube insertion device.

A mechanism for controlling the articulating joint J and thus for moving the distal end 12A may be controlled by any desired mechanism, such as a control device 268 as shown in FIG. 18 and described below. Alternatively, a control lever 57 be operatively attached to a handle 55, as shown in FIG. 15. If desired, a control device, such as the control lever 57, may be located at any other desired location on the introducing stylet 10, the handle 55, or on any other device attached to, or used with the introducing stylet 10 or the handle 55, such as a wireless remote controller, such as shown at W in FIG. 15.

It will be understood that the control lever 57 may be lengthened and configured such that it extends toward the distal end 12A (to the right when viewing FIG. 15) to a point intermediate the distal end 12A and the 15 mm ETT connector 32, i.e. a proximal end of the ETT 42, not shown in FIG. 15 clarity. Such a lengthened control lever 57 provides the user with easier, more direct access to the control lever 57 when inserting the introducing stylet 10 and the ETT 42 into the patient. Additionally, the lengthened control lever 57 may be configured as an attachable and detachable extension of the control lever 57 shown in FIG. 15, thus allowing the user to choose the desired length of the control lever 57.

FIG. 10 is an enlarged view of the distal end of a second embodiment of the introducing stylet 110. The introducing stylet 110 is substantially the same as the introducing stylet 10, except that the bridges 20 are formed at about a mid-point of the length of the Murphy eye plug 18.

FIG. 11 is an enlarged view of the distal end of a third embodiment of the introducing stylet 120. The introducing stylet 120 is substantially the same as the introducing stylet 110, except that the leading end of the distal end 120A has an increased leading length of about 20 mm as shown at D. The portion of the distal end 120A having the increased leading length D is substantially straight. Alternatively, the increased length D may be any desired length, such as between about 0.0 mm and about 30.0 mm. Additionally, if configured as a flexible bronchoscope for example, the length D may be about 100 mm.

Figure 13:
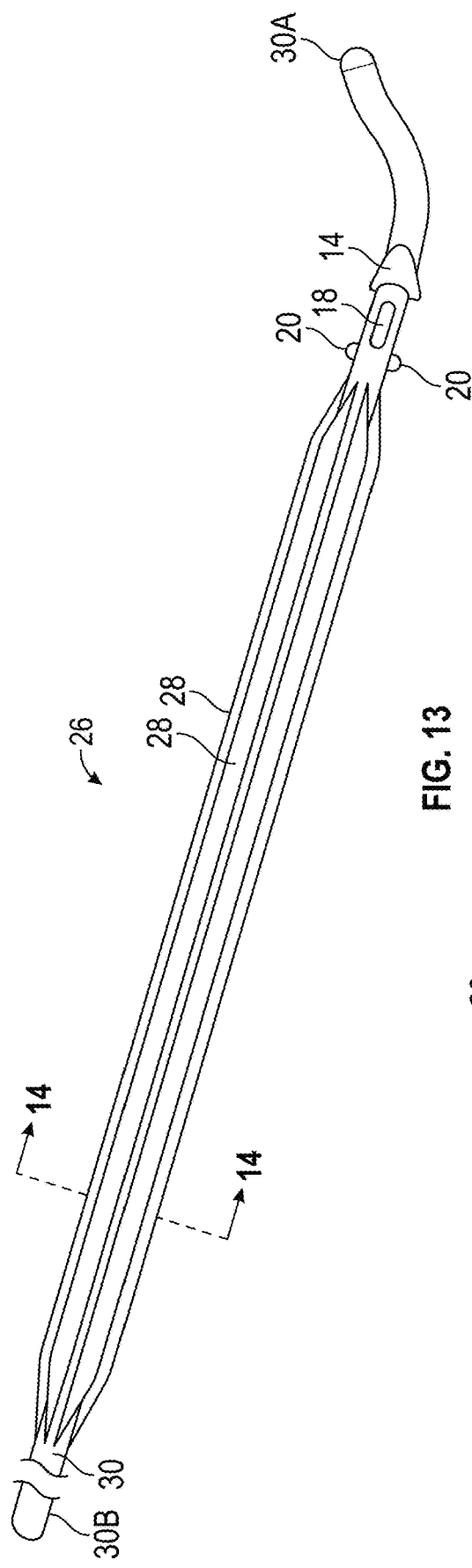
FIG. 13 is a perspective view of a fourth embodiment of the introducing stylet illustrated in FIGS. 1 through 9 showing the ribs.
Figure 14:
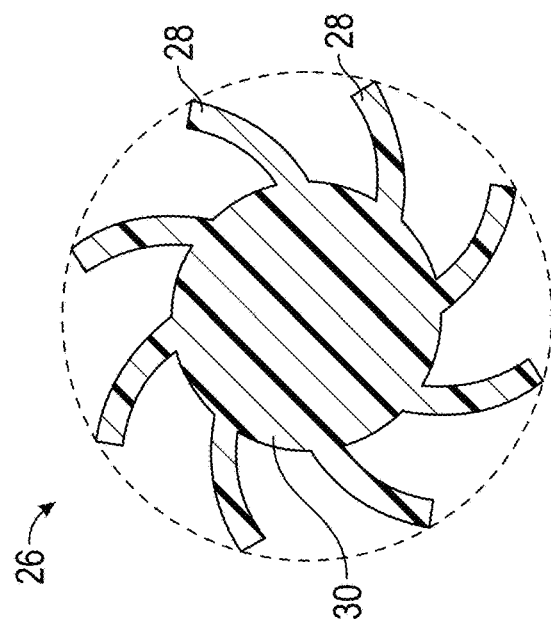
FIG. 14 is an enlarged cross-sectional view taken along the line 14-14 of FIG. 13.

As shown in FIGS. 13 and 14, a fourth embodiment of the introducing stylet is shown at 26. The exemplary introducing stylet 26 includes a plurality of ribs 28 extending longitudinally and radially outwardly of the elongated body 30. As shown in FIG. 14, the ribs 28 have an arcuate cross-sectional shape. Alternatively, the ribs 28 may have a non-arcuate cross-sectional shape, such as substantially straight. As described above, such ribs 28 having a non-arcuate cross-sectional shape also function as bridges.

The ribs 28 may be formed such that they extend for any desired length of the body 30 and may taper toward the distal end 30A and toward the proximal end 30B of the body 30. Additionally, the ribs 28 may be formed on only a portion of the circumference of the body 30. For example, the ribs 28 may be formed on about half or only about 180 degrees of the circumference of the body 30. Alternatively, the ribs 28 may be formed on any desired portion of the circumference of the body 30, such as between about 10 degrees and about 270 degrees of the circumference of the body 30.

The introducing stylet 26 may be otherwise similar to the introducing stylet 10 and include the overhanging obturating feature 14, the Murphy eye plug 18, and the plurality of semi-spherical bridges 20. Although not shown in FIGS. 13 and 14, the introducing stylet 26 may also include the longitudinally extending bore 22 formed therein and configured to have the elongated aluminum rod 24 may be mounted within the bore 22.

FIG. 15 is a right side view of the introducing stylet 10 shown with the conventional 15 mm ETT connector 32 and an oxygen source cap 54 mounted thereto, and a handle 55 at the proximal end 12B. The ETT 42 is not shown for clarity.

The illustrated 15 mm ETT connector 32 is a conventional ETT connector having a first embodiment of a flange 34. A first substantially cylindrical portion 36 extends outwardly from the flange 34 and is configured for attachment to a source of oxygen or air. A second substantially cylindrical portion 38 extends outwardly from the flange 34 opposite the first substantially cylindrical portion 36 and is configured for attachment to the ETT 42 such that the 15 mm ETT connector 32 is a removably attached component of the to the ETT 42, as described in detail above. An air passageway 40 is formed longitudinally through the 15 mm ETT connector 32.

The oxygen source cap 54 includes a body 56 having circumferentially extending wall 58 defining a generally cylindrical outside surface, an open first end 56A (the left end when viewing FIG. 15), and an open second end 56B (the right end when viewing FIG. 15). A longitudinally extending passageway (not shown) is formed through the body 56.

The illustrated oxygen source cap 54 includes means to attach the oxygen source cap 54 to the 15 mm ETT connector 32. In the illustrated embodiment, the means to attach the oxygen source cap 54 to the 15 mm ETT connector 32 is an attachment member that includes an elongated stylet positioning member 60, and resiliently mounted legs 74. The attachment member is configured to releasably attach the proximal end 12B of the rod 12 to the 15 mm ETT connector 32. Additionally, the second end 56B of the body 56 is mounted to the cylindrical portion 36 such that the cylindrical portion 36 is inserted into the longitudinally extending passageway (not shown) of the body 56 with an airtight, pressure-fit connection.

Alternatively, the second end 56B of the body 56 may have a reduced diameter portion (not shown) configured to be mounted within the open end of the cylindrical portion 36 with an airtight, pressure-fit connection. Advantageously, the airtight, pressure-fit connection between the second end 56B of the body 56 and the cylindrical portion 36 also allows the user to longitudinally and radially position the introducing stylet 10 relative to the 15 mm ETT connector 32 of the ETT 42.

Figure 17:
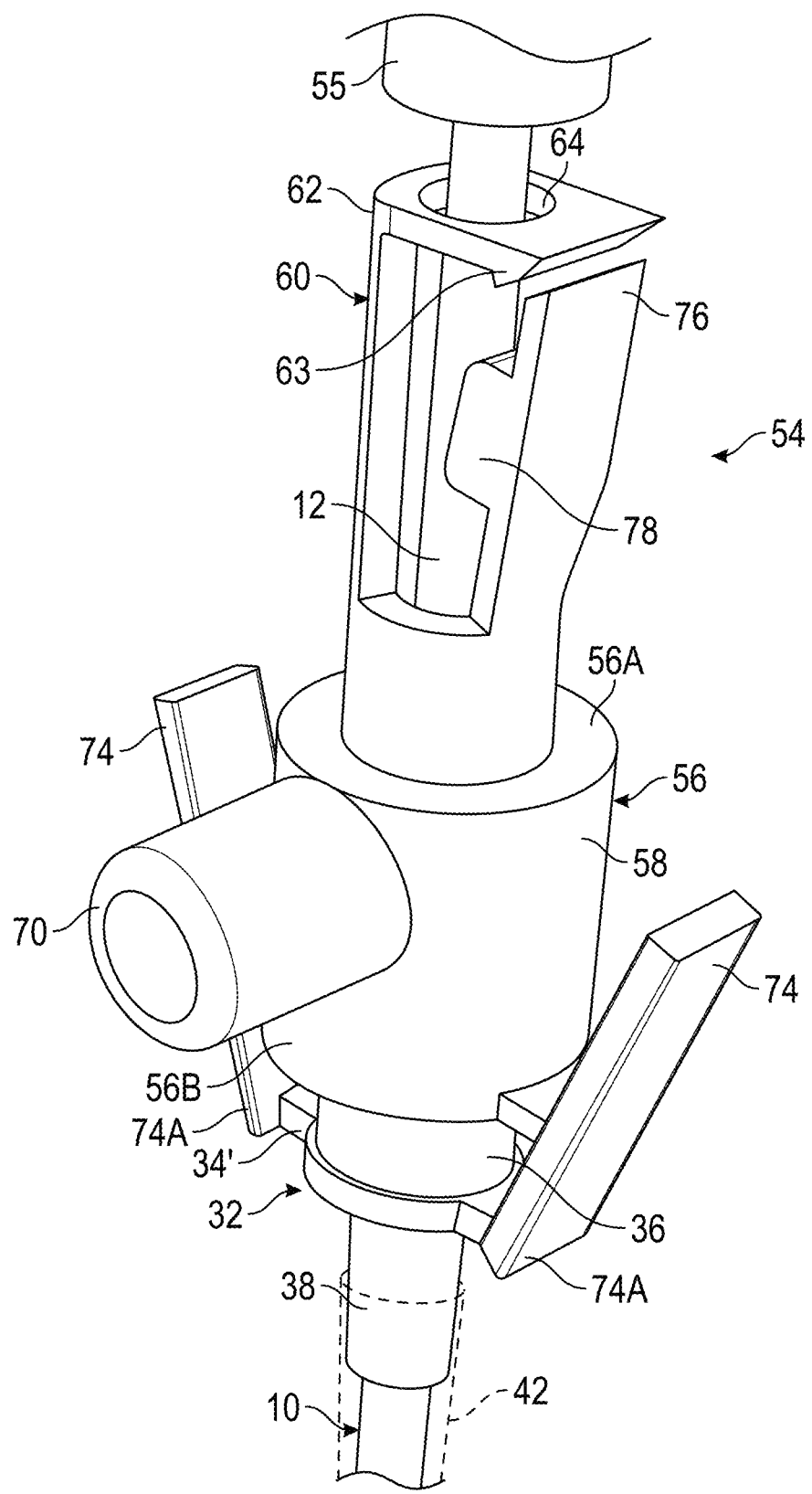
FIG. 17 is an enlarged perspective view of the ETT connector and the oxygen source cap illustrated in FIG. 15, shown mounted to the first embodiment of introducing stylet.

The elongated stylet positioning member 60 extends longitudinally outwardly from the first end 56A. The positioning member 60 includes an end wall 62 having stylet opening 64 formed therethrough and a lip 63 extending inwardly from a surface thereof (the downwardly facing surface when viewing FIG. 17).

Whether the second end 56B of the body is configured to be mounted within the passageway 40 of the 15 mm ETT connector 32, or about an outside surface of the cylindrical portion 36, at least a portion of an inside diameter of the longitudinally extending passageway (not shown) formed through the body 56 may be slightly smaller than an outside diameter of the rod 12. Thus, when the rod 12 extends through the longitudinally extending passageway (not shown) formed through the body 56, an airtight connection may be defined between the rod 12 and the body 56.

Figure 25:
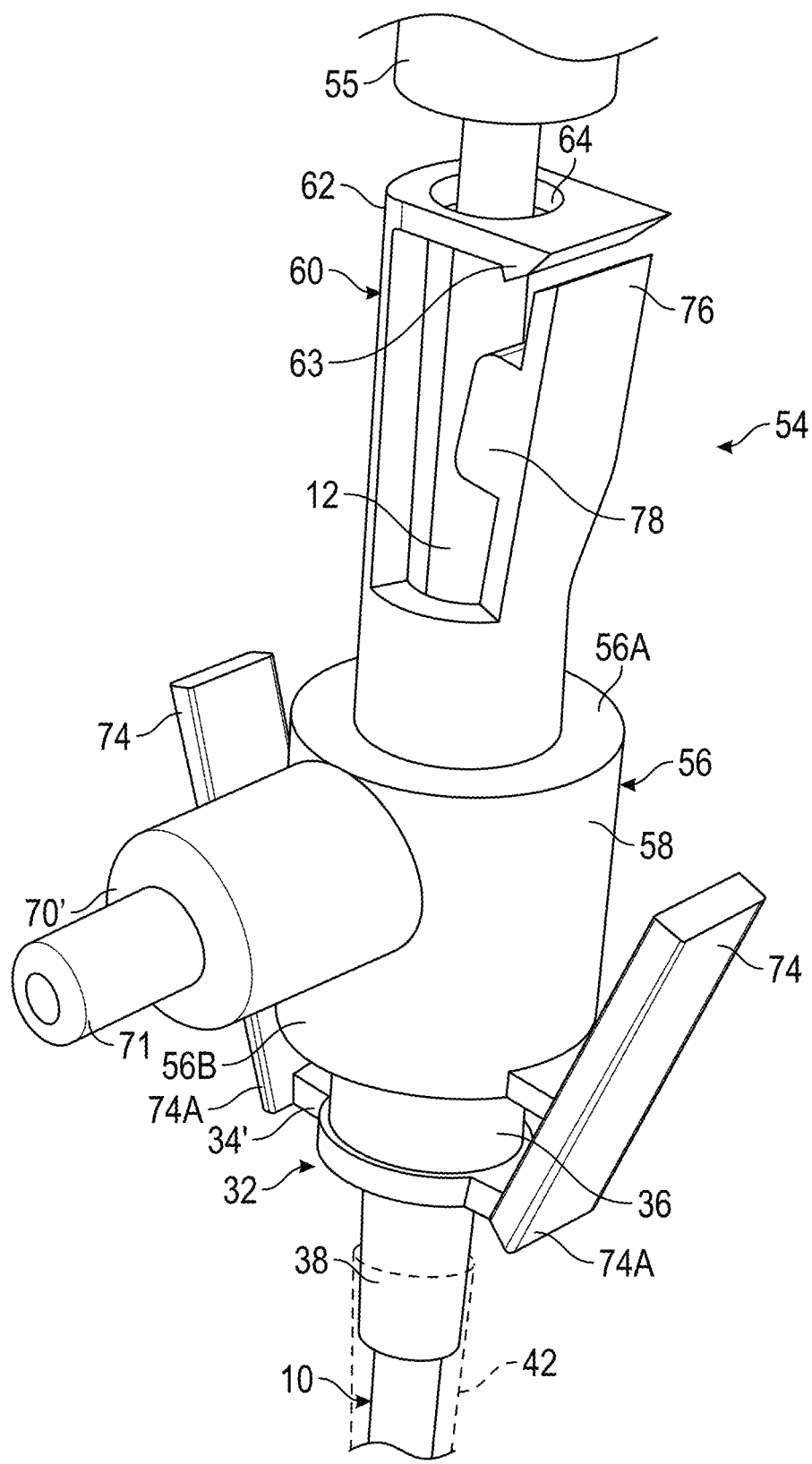
FIG. 25 is an enlarged perspective view of the ETT connector and the oxygen source cap illustrated in FIGS. 15 and 17, showing an alternate embodiment of the air inlet.

A generally cylindrical air inlet 70 extends radially outward of the circumferentially extending wall 58 and is in fluid communication with the open second end 56B of the oxygen source cap 54. The air inlet 70 may be connected to any desired source of oxygen, schematically illustrated at 72 in FIG. 15, such as for example a direct line oxygen source. Preferably, the air inlet 70 has a 15 mm outside diameter, thus replicating the 15 mm connection of the conventional 15 mm ETT connector 32. As shown in FIG. 25, the air inlet 70' may include a longitudinally extending reduced diameter portion 71 having a 6 mm outside diameter, thus allowing conventional 6 mm line tubing to also be connected to the air inlet 70' via the reduced diameter portion 71. Alternatively, the air inlet 70 may have any other desired shape or size, such as a conventional 6 mm line tubing Christmas tree connector (not shown) or a conventional nipple adapter (not shown). If desired, the air inlet 70 may be provided with an air-tight cap (not shown) to prevent retrograde air flow when the assembly shown in FIG. 15 is used with another device, such as a supraglottic airway (SGA) (not shown) or a laryngeal mask airway (not shown).

If desired, the oxygen source cap 54 may be formed as a positioning cap (not shown) without the air inlet 70, thus allowing such a positioning cap (not shown) to be used as a proximal longitudinal positioning cap. Further, the positioning cap (not shown) that is formed without the air inlet 70 may also be formed with any desired number of the features described herein for connecting the introducing stylet 10 to the 15 mm ETT connector 32, such as the elongated stylet positioning member 60, the resiliently mounted legs 74, the airtight connection defined between the rod 12 and the body 56, and the airtight, pressure-fit connection between the second end 56B of the body 56 and the cylindrical portion 36 of the 15 mm ETT connector 32. Advantageously, when formed as the positioning cap without the air inlet 70, the embodiment wherein the second end 56B of the body 56 has a reduced diameter portion (not shown) that is mounted within the open end of the cylindrical portion 36 with an airtight, pressure-fit connection further functions to improve the airtight connection between body 56 and the rod 12.

Additionally, the introducing stylet 10 may include a connector (not shown) or other device that connects the introducing stylet 10 to the SGA (not shown). The connector (not shown) may be configured as a support bracket, a clamp, a rail, and the like. The connector (not shown) may also be rigid, fixed, telescoping, or hinged or otherwise foldable so as to allow the user to change the relative distance between the introducing stylet 10 and SGA (not shown).

When in use, the oxygen source cap 54 may be urged into contact with the 15 mm ETT connector 32 such that the second substantially cylindrical portion 36 of the 15 mm ETT connector 32 is inserted into the open second end 56B of the oxygen source cap 54 and attached in a press-fit arrangement. Oxygen from the source of oxygen 72 may then flow through the oxygen source cap 54 into the ETT 42. The rod 12 extends through the longitudinally extending passageway (not shown) formed through the body 56 and defines an airtight connection between the rod 12 and the body 56.

The resiliently mounted legs 74 are attached to the second end 56B of the oxygen source cap 54 and define attachment members. Distal ends 74A of the legs 74 are configured to engage a second embodiment of the flange 34', thus attaching the oxygen source cap 54 to the 15 mm ETT connector 32.

The stylet positioning member 60 includes a longitudinally extending locking arm 76 having a stylet engagement member 78 formed thereon. In operation, the oxygen source cap 54 is positioned at a desired position relative to the introducing stylet 10. The stylet engagement member 78 is then urged into contact with the rod 12 of the introducing stylet 10 and a proximal end of the locking arm 76 is urged inwardly into a snap-fit connection with the lip 63 of the end wall 62, thus temporarily attaching the oxygen source cap 54 to the introducing stylet 10. The oxygen source cap 54 may be formed from any suitable polymer, such as but not limited to polylactide (PLA), polyvinylchloride (PVC), and polyurethane.

Alternatively, the means to attach the oxygen source cap 54 to the 15 mm ETT connector 32 may include a squeeze pressure mechanism (not shown) to position the ETT 42, preferably via the 15 mm ETT connector 32 at a plurality of positions on the rod 12 of the introducing stylet 10.

Figure 2:
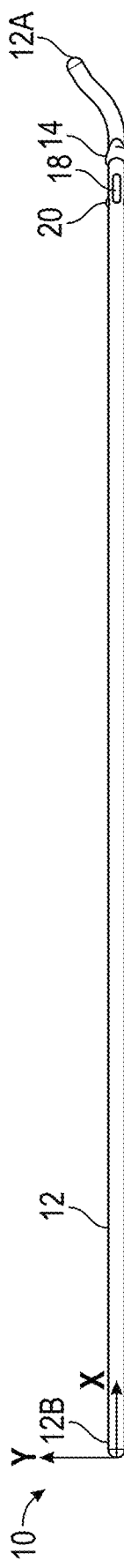
FIG. 2 is right side view of the introducing stylet illustrated in FIG. 1.
Figure 3:
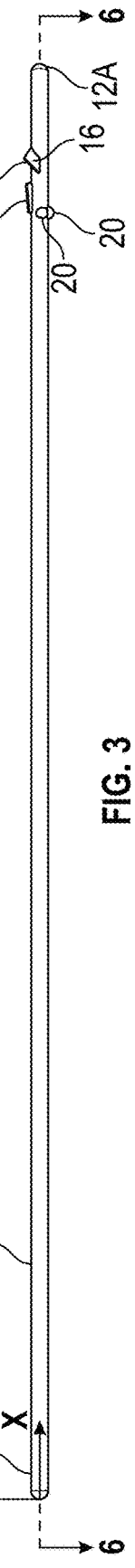
FIG. 3 is a bottom view of the introducing stylet illustrated in FIGS. 1 and 2.
Figure 4:
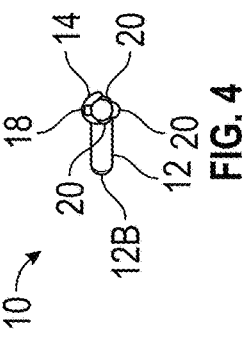
FIG. 4 is a proximal end view of the introducing stylet illustrated in FIGS. 1 through 3.
Figure 5:
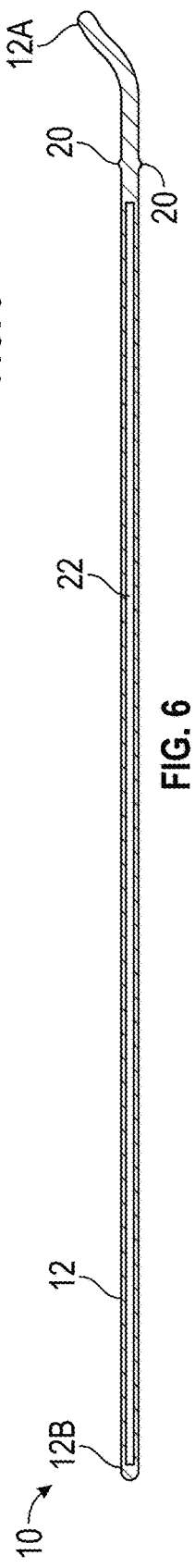
FIG. 5 is a distal end view of the introducing stylet illustrated in FIGS. 1 through 4.
Figure 19:
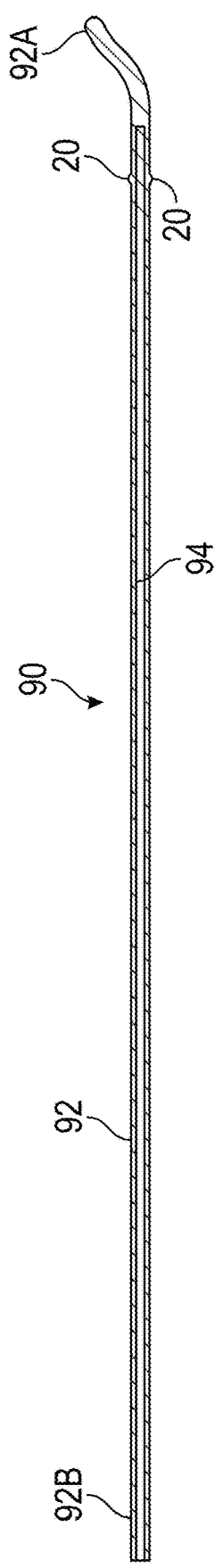
FIG. 19 is a cross-sectional view of a fifth embodiment of the introducing stylet configured as a sheath.

Referring now to FIG. 19, a fifth embodiment of the introducing stylet is shown at 90. The introducing stylet is configured as a sheath 90. The sheath 90 is similar to the introducing stylet 10 and includes an elongated body configured as a rod 92. The rod 92 is substantially cylindrical and has a closed first or distal end 92A and an open second or proximal end 92B. The distal end 92A of the sheath 90 may be substantially the same as the distal end 12A of the introducing stylet 10 and have the soft S-shape with a rounded or semi-spherical distal tip. The distal end 92A may also include one or more of the semi-spherical bridges 20 (shown in FIG. 19), and the overhanging obturating feature 14 and the Murphy eye plug 18, as best shown in FIGS. 1 through 3 and described in detail above. The distal end 92A may be formed with any combination of the bridges 20, the overhanging obturating feature 14, and the Murphy eye plug 18. It will be understood that not all of the bridges 20, the overhanging obturating feature 14, and the Murphy eye plug 18 are required and that the distal end 92A may be formed with any one or more of these features. It will be further understood that the overhanging obturating features 14 and 214, and the Murphy eye plug 18 may have colored or other indicia to assist the user in positioning the introducing stylet 10.

Like the introducing stylet 10, the sheath 90, including the distal end 92A thereof, may be formed from any flexible or semi-flexible material, such as silicon, rubber, and other polymers.

A longitudinally extending bore 94 may be formed in the sheath 90 and have diameter configured to have a conventional scope or tube exchanger, such as a flexible bronchoscope (not shown) inserted therein. Although the sheath 90 is illustrated having a closed distal end 92A, it will be understood that the distal end 92A may be open, and may have a flexible straight distal tip corresponding to the shape of a conventional flexible bronchoscope, such as for example to accommodate a conventional scope with an imaging device at a distal end thereof.

It will be understood that the distal end 92A of the sheath 90, like the distal end 12A of the rod 12 of the introducing stylet 10, may have a shape other than the illustrated soft S-shape. For example, the distal end 92A may be substantially straight, may have one bend or more than the two bends illustrated. The bends may be formed in any radial direction.

Figure 20:
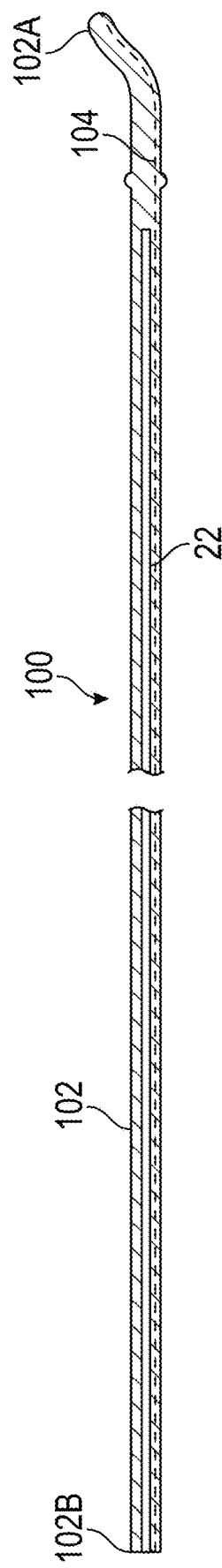
FIG. 20 is a cross-sectional view of a sixth embodiment of the introducing stylet showing an air flow passageway formed longitudinally therethrough.

Referring now to FIG. 20, a sixth embodiment of the introducing stylet is shown at 100. The introducing stylet 100 is substantially the same as the introducing stylet 10 and includes an elongated body configured as a rod 102. The rod 102 is substantially cylindrical and has a first or distal end 102A, a second or proximal end 102B, and may have the bore 22. The distal end 102A of the introducing stylet 100 may be substantially the same as the distal end 12A of the introducing stylet 10 and have the soft S-shape with a rounded or semi-spherical distal tip. The distal end 102A may also include one or more of the semi-spherical bridges 20 (shown in FIG. 19), and the overhanging obturating feature 14 and the Murphy eye plug 18, as best shown in FIGS. 1 through 3 and described in detail above. Like the introducing stylet 10, the introducing stylet 100, including the distal end 102A thereof, may be formed from any flexible or semi-flexible material, such as silicon, rubber, and other polymers, such as any polymers used to form conventional flexible bronchoscopes.

Additionally, the introducing stylet 100 includes one or more internal and fully circumferentially enclosed air flow passageways, one of which is schematically illustrated at 104, formed longitudinally therethrough from the proximal end 102B to the distal end 102A. The air flow passageway 104 provides air flow to the patient during insertion of the introducing stylet 100. Additionally, the one or more passageways 104 may be configured as a suction tube and may therefore be connected to a vacuum port (not shown). Further, the one or more passageways 104 may be configured as a passageway for the insertion and use of a guidewire in an endotracheal tube insertion device, such as described in U.S. Pat. No. 7,563,227 to Gardner, the disclosure of which in incorporated herein in its entirety. The air flow passageways 104 may have any desired diameter, such as about 3.0 mm. Alternatively, the air flow passageways 104 may have any desired diameter, such as within the range of about 1.0 mm to about 4.0 mm.

Referring now to the drawings, an embodiment of a known endotracheal tube insertion device is indicated generally at 230 in FIG. 18. FIG. 2 of U.S. Pat. No. 9,949,629 is reproduced herein as FIG. 18. The illustrated laryngoscope 230 is described in U.S. Pat. No. 9,949,629 to Gardner, the disclosure of which in incorporated herein in its entirety.

It will be understood that all of the embodiments of the introducing stylets described herein may be used with the endotracheal tube insertion device 230 in lieu of the rod 272. The illustrated endotracheal tube insertion device is configured to allow the user to simultaneously open the airway, view a patient's airway, accurately position the ETT 42 (also shown in FIG. 16) within the airway, and transmit a video image of the patient's airway. The embodiments of the introducing stylets described herein may thus be configured to be connected to the blade 235, the optical channel member 237, the optical assembly 236, or any component of the optical assembly 236, such as the optical housing 250 and the flexible member, of the laryngoscope 230 illustrated in FIG. 18, or similar laryngoscope.

The illustrated endotracheal tube insertion device 230 includes a handle 232 attached to a blade assembly 234, an optical assembly 236, and a guided introducer intubation assembly 238. The handle 232 is configured to be gripped by the hand of the user of the endotracheal tube insertion device 230.

A video monitor 240 is attached to a proximal end of the optical assembly 236 and is operationally connected to a video imaging device (not shown) within the optical assembly 236. In the illustrated embodiment, the video monitor 240 is mounted to a flexible member (not shown). The video monitor 240 may also be releasably attached to the optical assembly 236 for remote viewing at a distance from the patient. Further, one or more additional video monitors 240 (not shown) may be positioned remotely from the endotracheal tube insertion device 230 and connected thereto by a wired or a wireless connection. Alternatively, the video monitor 240 may also be attached, including releasably attached, to the handle 232. In the illustrated embodiment, the video monitor has a substantially rectangular shape. Alternatively, the video monitor 240 may have any desired shape and size.

The handle 232 may also include a processor or controller 233 with Wi-Fi, or local area wireless technology that allows the endotracheal tube insertion device 230 to participate in computer networking. The processor or controller 233 may also have Bluetooth capability to allow a medical specialist to view, via the internet, any video images captured by the optical assembly 236. If desired, the controller 233 may be provided as a part of the video monitor 240, or at any other desired location in the improved endotracheal tube insertion device 230. Alternatively, in lieu of the handle 232, the handle and viewing member described in U.S. Pat. No. 7,563,227 may be provided. The disclosure of U.S. Pat. No. 7,563,227 in incorporated herein in its entirety.

The blade assembly 234 has an insertion member configured as an elongated blade 235 attached to a channel member 237. The elongated blade 235 includes a first or distal end 235a, and a second or proximal end (not shown) attached to the handle 232.

The channel member 237 includes a first or distal end, a second or proximal end, defines a longitudinally extending channel, and is attached to a first side or lower side of the blade body 235. The channel member 237 is substantially C-shaped when viewed in cross-section and defines an elongated slot 237b that provides access to the channel within the channel member 237. Alternatively, the channel member 237 may have any desired cross-sectional shape, such as substantially oval, and substantially rectangular.

If desired, endotracheal tube retention tabs may be provided on the blade assembly 234 of the endotracheal tube insertion device 230. For example, as shown in FIG. 18, two endotracheal tube retention tabs 239a extend outwardly and upwardly (when viewing FIG. 18) from the channel member 237 and one endotracheal tube retention tab 239b extends outwardly and downwardly (when viewing FIG. 18) from the handle 232. The endotracheal tube retention tabs 239a and 239b have a generally arcuate shape and are configured to allow the ETT 42 to be temporarily positioned and retained between the endotracheal tube retention tabs 239a and the endotracheal tube retention tab 239b. Alternatively, the tracheal tube retention tabs 239a and 239b may have any other desired shape suitable for retaining the ETT 42. Like the blade 235 and the channel member 237, the endotracheal tube retention tabs 239a and 239b may be formed from any desired rigid or semi-rigid material, such as stainless steel and polyvinyl chloride (PVC). It will be understood that any desired number of endotracheal tube retention tabs 239a and 239b may be provided. Further, the endotracheal tube retention tabs 239a and 239b may be provided at any desired location on the blade assembly 234 and/or the handle 232.

As shown in FIG. 18, the optical assembly 236 is disposed within the channel of the channel member 237. The optical assembly 236 includes an optical housing 250 and a flexible member (not shown).

A mechanism for moving a portion of the distal end of the flexible member (not shown) may be controlled by a control device 268 having a rotatable knob 268a. An attachment member 270 is attached to a mounting post (not shown) of the control device 268. The attachment member 270 may be any device configured to retain the guided introducer intubation assembly 238 and its attached ETT 42, described below, relative to the endotracheal tube insertion device 230, and more specifically relative to the flexible member (not shown).

The guided introducer intubation assembly 238 includes an intubation assembly body configured as a rod 272, which defines an introducer or bougie. The rod 272 is substantially cylindrical and has an elongated body having a first or distal end 272a and a second or proximal end 272b.

The proximal end 272b of the rod 272 includes threads 273 configured for connecting the rod 272 to a first or proximal connecting member 282. The first connecting member 282 includes a base 284 having a plurality of arms 286 extending outward therefrom. The arms 286 include inwardly extending flanges or locking members 288. A substantially cylindrical body 290 also extends outwardly from the base 284 between the arms 286. A longitudinally extending threaded channel (not shown) is formed at least through the base 284. The first connecting member 282 is configured to be attached to the threads 273 of the rod 272. This threaded connection allows the user to adjust the longitudinal position of the first connecting member 282 relative to the rod 272. This threaded connection further allows the user to shorten or lengthen the rod 272 relative to the length of the ETT 42 that will be mounted on the rod 272.

The illustrated rod 272 includes a guide system configured to guide the ETT 42 into the trachea, and configured for releasable attachment to the 24 member (not shown). In the illustrated embodiment, the guide system is a guide rail 275. The illustrated guide rail 275 includes a substantially spherical tip 276 at a distal end thereof. It will be understood that any of the embodiments of the introducing stylets described and illustrated herein may include any of the guide systems described in U.S. Pat. No. 9,949,629.

It will be further understood that all of the embodiments of the introducing stylets described herein may also be used with a supraglottic type insertion device, such as the ETT insertion device 330 having the supraglottic portion 332 as shown in FIG. 20, and the ETT insertion device 700 having the supraglottic cuff 706 disclosed in U.S. Pat. No. 9,949,629. For example, the embodiments of the introducing stylets described herein may be used with a housing similar to the housing portion 350 shown in FIG. 20 or with a channel member similar to the channel member 720 shown in FIG. 41.

The principle and mode of operation of this invention have been explained and illustrated in its preferred embodiments. However, it must be understood that this invention may be practiced otherwise than as specifically explained and illustrated without departing from its spirit or scope.

What is claimed is:

1. An introducing stylet assembly comprising:
   an endotracheal tube (ETT);
   an introducing stylet comprising an elongated rod, the elongated rod having a distal end and a proximal end;
   a bridge formed on the elongated rod and configured to engage an inside surface of the ETT into which the introducing stylet has been inserted, to prevent both longitudinal and lateral movement of the introducing stylet relative to the ETT;
   wherein an air flow path is defined adjacent the bridge between the inside surface of the ETT and the elongated rod, the air flow path thus ensuring that air flow is maintained through the ETT;
   an overhanging obturating feature extending circumferentially about a portion of the elongated rod and including a tapered leading surface, a flat trailing surface, and an arcuate edge formed between the leading surface and the trailing surface, the arcuate edge defining a plane extending transversely to a longitudinal axis of the elongated rod and further defining an ETT-engaging surface, wherein the obturating feature is configured to occlude a gap that would otherwise exist between a flat leading surface of a portion of a bevel of the ETT and the obturating feature, and wherein the flat trailing surface abuts a leading end of the ETT; and
a Murphy eye plug formed on the elongated rod proximal of the overhanging obturating feature, and positioned within a Murphy eye of the ETT;
wherein a portion of the distal end of the elongated rod extends longitudinally outwardly of the ETT and defines a leading end.

2. The introducing stylet assembly according to claim 1, further including at least one internal and circumferentially enclosed air flow passageway formed longitudinally through the elongated rod from the proximal end to the distal end.

3. The introducing stylet assembly according to claim 1, wherein the bridge is one of a semi-spherical bridge and an elongated, longitudinally extending bridge configured to engage the inside surface of the ETT.

4. The introducing stylet assembly according to claim 3, further including an elongated, malleable rod within a longitudinally extending bore.

5. The introducing stylet assembly according to claim 1, wherein the leading end of the elongated rod has at least one bend formed therein.

6. The introducing stylet assembly according to claim 1, wherein the leading end of the elongated rod is formed with two bends defining a soft S-shape.

7. The introducing stylet assembly according to claim 6, further including at least one internal and circumferentially enclosed air flow passageway formed longitudinally through the elongated rod from the proximal end to the distal end.

8. The introducing stylet assembly according to claim 1, wherein the bridge comprises a plurality of bridges.

9. The introducing stylet assembly according to claim 1 further including an attachment member defining a cap and configured to releasably attach the proximal end of the elongated rod to a 15 mm ETT connector.

10. The introducing stylet assembly according to claim 9, wherein the cap is an oxygen source cap mounted to the 15 mm ETT connector of the ETT, wherein the oxygen source cap includes:
a body having a circumferentially extending wall defining a cylindrical outside surface, a first end, and an open second end; and
a cylindrical air inlet that extends radially outward of the circumferentially extending wall, is in fluid communication with the open second end of the oxygen source cap, and is configured for connection to a source of oxygen; and
wherein the elongated rod of the introducing stylet extends through the connected oxygen source cap and 15 mm ETT connector of the ETT such that the oxygen source cap is connected to the introducing stylet with an airtight connection.

11. The introducing stylet assembly according to claim 10, further including resiliently mounted legs attached to the second end of the oxygen source cap body and defining attachment members, wherein distal ends of the legs are configured to engage a flange of the 15 mm ETT connector, thus releasably attaching the oxygen source cap to the 15 mm ETT connector.

12. The introducing stylet assembly according to claim 9, further including:
a handle at the proximal end of the elongated rod;
an articulating joint at one or more locations on the introducing stylet;
a mechanism for controlling the articulating joint; and
a control lever that is one of: (a) connected to the handle and to the mechanism for controlling the articulating joint and (b) wirelessly connected to the mechanism for controlling the articulating joint, the control lever configured to control movement of the articulating joint.

13. The introducing stylet assembly according to claim 12, wherein the obturating feature is one of inflatable and formed from a plurality of longitudinally and radially outwardly extending compressible ribs.

14. The introducing stylet assembly according to claim 9, further including a video imaging device mounted in a distal tip of the introducing stylet;
wherein the video imaging device is operationally connected to a video monitor.

15. The introducing stylet assembly according to claim 1, wherein the obturating feature is one of inflatable and formed from a plurality of longitudinally and radially outwardly extending compressible ribs.

16. The introducing stylet assembly according to claim 1, wherein the proximal end of the elongated rod includes threads configured for connecting the elongated rod to a proximal connecting member.

17. The introducing stylet assembly according to claim 1, wherein the introducing stylet is configured for use with one of a supraglottic type insertion device and an optical assembly of an ETT insertion device having a blade.

18. An introducing stylet assembly comprising:
an endotracheal tube (ETT);
an introducing stylet comprising an elongated rod, the elongated rod having a distal end and a proximal end;
a bridge extending radially outward of the elongated rod at the distal end thereof and proximal of a distal tip of an ETT into which the introducing stylet has been inserted the bridge configured to prevent both longitudinal and lateral movement of the introducing stylet relative to the ETT;
wherein an air flow path is defined adjacent the bridge between the inside surface of the ETT and the elongated rod, the air flow path thus ensuring that air flow is maintained through the ETT;
an elongated, malleable rod within a longitudinally extending bore;
an obturating feature extending circumferentially about a portion of the elongated rod and including a tapered leading surface, a flat trailing surface, and an arcuate edge formed between the leading surface and the trailing surface, the arcuate edge defining a plane extending transversely to a longitudinal axis of the elongated rod and further defining an ETT-engaging surface, wherein the obturating feature is configured to occlude a gap that would otherwise exist between a flat leading surface of a portion of a bevel of the ETT and the obturating feature, and wherein the flat trailing surface abuts a leading end of the ETT;
a Murphy eye plug formed on the elongated rod proximal of the obturating feature, and positioned within a Murphy eye of the ETT;
an oxygen source cap mounted to a 15 mm ETT connector of the ETT, wherein the oxygen source cap includes:

a body having a circumferentially extending wall defining a cylindrical outside surface, a first end, and an open second end;
a cylindrical air inlet extending radially outward of the circumferentially extending wall, wherein the air inlet is in fluid communication with the open second end of the oxygen source cap and is configured for connection to a source of oxygen;
means to releasably attach the oxygen source cap to the 15 mm ETT connector; and
an attachment member configured to releasably attach the proximal end of the elongated rod to the 15 mm connector;
wherein the elongated rod of the introducing stylet extends through the connected oxygen source cap and 15 mm ETT connector of the ETT such that the oxygen source cap is connected to the introducing stylet with an airtight connection;
wherein a portion of the distal end of the elongated rod that extends longitudinally outwardly of the obturating feature defines a leading end;
wherein the bridge is configured to engage an inside surface of the ETT to prevent both longitudinal and lateral movement of the introducing stylet relative to the ETT; and
wherein the leading end of the elongated rod is formed with two bends defining a soft S-shape.

19. The introducing stylet assembly according to claim 18, further including:
a handle at the proximal end of the elongated rod;
an articulating joint at one or more locations on the introducing stylet;
a mechanism for controlling the articulating joint;
a control lever that is one of: (a) connected to the handle and to the mechanism for controlling the articulating joint and (b) wirelessly connected to the mechanism for controlling the articulating joint, the control lever configured to control movement of the articulating joint; and
a video imaging device mounted in a distal tip of the introducing stylet;
wherein the video imaging device is operationally connected to a video monitor.

20. An introducing stylet assembly comprising:
an endotracheal tube (ETT);
an introducing stylet comprising an elongated rod, the elongated rod having a distal end and a proximal end;
a semi-spherical bridge formed on the elongated rod and configured to engage an inside surface of the ETT into which the introducing stylet has been inserted, to prevent both longitudinal and lateral movement of the introducing stylet relative to the ETT;
wherein an air flow path is defined adjacent the bridge between the inside surface of the ETT and the elongated rod, the air flow path thus ensuring that air flow is maintained through the ETT;
an obturating feature configured as a protruding portion of the distal end of the elongated rod, wherein a widest point of the obturating feature, when measured transversely from an axis of the elongated rod, does not extend transversely outward of an inside surface of the ETT, and is configured to abut the inside surface of the ETT; and
a Murphy eye plug formed on the elongated rod proximal of the obturating feature, and positioned within a Murphy eye of the ETT;
wherein a portion of the distal end of the elongated rod extends longitudinally outwardly of the ETT and defines a leading end.

21. An introducing stylet configured for insertion into a human trachea, the introducing stylet comprising:
an elongated rod, the elongated rod having a distal end and a proximal end;
a semi-spherical bridge formed on the distal end of the elongated rod and configured to engage an inside surface of an endotracheal tube (ETT) into which the introducing stylet has been inserted, to prevent both longitudinal and lateral movement of the introducing stylet relative to the ETT; an obturating feature extending circumferentially about a portion of the elongated rod and including a tapered leading surface, a flat trailing surface, and an arcuate edge formed between the leading surface and the trailing surface, the arcuate edge defining a plane extending transversely to a longitudinal axis of the elongated rod, wherein the obturating feature is configured to occlude a gap that would otherwise exist between a flat leading surface of a portion of a bevel of the ETT and the obturating feature, and wherein the flat trailing surface abuts a leading end of the ETT; and a Murphy eye plug formed on the elongated rod proximal of the obturating feature.

* * * * *

UNITED STATES PATENT AND TRADEMARK OFFICE
CERTIFICATE OF CORRECTION

Page 1 of 1

PATENT NO. : 10,758,708 B2
APPLICATION NO. : 16/671474
DATED : September 1, 2020
INVENTOR(S) : Glenn P. Gardner It is certified that error appears in the above-identified patent and that said Letters Patent is hereby corrected as shown below:

In the Claims

Column 18, Claim 18, Line 42, reads:
"inserted the bridge configured to prevent both longitu-"

Should read:
--inserted, the bridge configured to prevent both longitu- --

Signed and Sealed this
Twentieth Day of October, 2020

Andrei Iancu
*Director of the United States Patent and Trademark Office*